(12) United States Patent
Calvert et al.

(10) Patent No.: US 7,232,680 B2
(45) Date of Patent: *Jun. 19, 2007

(54) INFECTIOUS CDNA CLONE OF NORTH AMERICAN PORCINE REPRODUCTIVE AND RESPIRATORY SYNDROME (PRRS) VIRUS AND USES THEREOF

(75) Inventors: Jay G. Calvert, Gales Ferry, CT (US); Michael G. Sheppard, North Stonington, CT (US); Siao-Kun W. Welch, North Stonington, CT (US)

(73) Assignee: Pfizer Inc., New York, NY (US)

( * ) Notice: Subject to any disclaimer, the term of this patent is extended or adjusted under 35 U.S.C. 154(b) by 788 days.

This patent is subject to a terminal disclaimer.

(21) Appl. No.: 10/127,391

(22) Filed: Apr. 22, 2002

(65) Prior Publication Data

US 2002/0172690 A1  Nov. 21, 2002

Related U.S. Application Data

(63) Continuation of application No. 09/470,661, filed on Dec. 22, 1999, now Pat. No. 6,500,662.

(60) Provisional application No. 60/113,345, filed on Dec. 22, 1998.

(51) Int. Cl.
  *C12N 7/00* (2006.01)
  *C12N 7/01* (2006.01)
  *C12N 7/02* (2006.01)
  C12P 21/00 (2006.01)
  C07H 21/04 (2006.01)

(52) U.S. Cl. .................. 435/235.1; 435/69.1; 435/239; 424/93.6

(58) Field of Classification Search ............ 435/235.1, 435/239, 325, 69.1, 69.3, 320.1; 536/23.1, 536/23.7, 25.72, 24.1; 424/184.1, 204.1
See application file for complete search history.

(56) References Cited

U.S. PATENT DOCUMENTS

| | | | |
|---|---|---|---|
| 3,137,631 | A | 6/1964 | Soloway |
| 3,959,457 | A | 5/1976 | Speaker et al. |
| 4,015,100 | A | 3/1977 | Gnanamuthu et al. |
| 4,205,060 | A | 5/1980 | Monsimer et al. |
| 4,452,747 | A | 6/1984 | Gersonde et al. |
| 4,606,940 | A | 8/1986 | Frank et al. |
| 4,744,933 | A | 5/1988 | Rha et al. |
| 4,921,706 | A | 5/1990 | Roberts et al. |
| 4,927,637 | A | 5/1990 | Morano et al. |
| 4,944,948 | A | 7/1990 | Uster et al. |
| 5,008,050 | A | 4/1991 | Cullis et al. |
| 5,009,956 | A | 4/1991 | Baumann |
| 5,132,117 | A | 7/1992 | Speaker et al. |
| 6,268,199 | B1 * | 7/2001 | Meulenberg et al. .... 435/235.1 |
| 6,977,078 | B2 * | 12/2005 | Paul et al. ............... 424/204.1 |

FOREIGN PATENT DOCUMENTS

| | | |
|---|---|---|
| WO | WO 92/21375 | 12/1992 |
| WO | WO 93/03760 | 3/1993 |
| WO | WO 95/28227 | 10/1995 |
| WO | WO 96/06619 A1 | 3/1996 |
| WO | WO 98/18933 * | 5/1998 |

OTHER PUBLICATIONS

Blast Alignments (Acession AF494042 with Accessions U20788 and U030400, 2005.*
GeneBank U87392, Porcine reproductive and respiratory syndrome virus strain VR-2332, complete genome, including Revision History, 1998.*
Meng et al. Journal of General Virology, 75: 1795-1801, (1994).*
Murtaugh et al., Archives of Virology, vol. 140 No. 8, pp. 1451-1460 (1995).*
Toepfer-berg et al., Journal of Animal Science, vol. 82 No. 7, pp. 1942-195 (Jul. 2004).*
Bowie et al., Science, vol. 247 No. 4948. pp. 1306-1310 (Mar. 1990).*

(Continued)

*Primary Examiner*—Bruce R. Campell
*Assistant Examiner*—Zachariah Lucas
(74) *Attorney, Agent, or Firm*—Thomas A. Wootton

(57) ABSTRACT

The invention provides isolated polynucleotide molecules, including plasmids; viral vectors; and transfected host cells that comprise a DNA sequence encoding an infectious RNA sequence encoding a North American PRRS virus; and also North American PRRS viruses encoded thereby. The invention further provides isolated infectious RNA molecules encoding a North American PRRS virus. The invention also provides isolated polynucleotide molecules, infectious RNA molecules, viral vectors, and transfected host cells encoding genetically-modified North American PRRS viruses; and genetically-modified North American PRRS viruses encoded thereby. The invention also provides vaccines comprising such plasmids, RNA molecules, viral vectors, and North American PRRS viruses, and methods of using these vaccines in swine and in other animals. Also provided are isolated polynucleotide molecules, viral vectors, and transfected host cells that comprise a nucleotide sequence encoding a peptide of a North American PRRS virus. These viral vectors and transfected host cell lines are useful in providing peptides to compensate for mutated peptide coding sequences of DNA sequences encoding genetically-modified North American PRRS viruses so that functional virions can be generated.

2 Claims, 2 Drawing Sheets

OTHER PUBLICATIONS

Yoo et al., Veterinary Immunology and Immunopathology, vol. 103 No. 3, pp. 143-154 (Dec. 2004).*

Andreyev VG., Wesley RD., Mengeling WL., Vorwald AC., Lager KM., Genetic variation and phylogenetic relationships of 22 porcine reproductive and respiratory syndrome virus (PRRSV) field starins based on sequence analysis of open reading frame 5, Arch Virol 142:993-1001, 1997.

Ausubel et al., 1989, Current Protocols in Molecular Biology, Greene Publishing Associates & Wiley Interscience, NY.

Collins JE., Benfield DA., Christianson WT., Harris L., Hennings JC., Shaw DP., Goyal SM., McCullough S., Morrison RB., Joo HS., Gorcyca D., Chladek D. Isolation of swine infertility and respiratory syndrome virus (isolate ATCC VR-2332) in North America and experimental reproduction of the disease in gnotobiotic pigs, J Vet Diagn Invest 4:117-126, 1992.

A. Domb et al., 1992, Polymers for Advanced Technologies, 3:279-292.

Kim HS., Kwang J., Yoon IJ., Joo HS., Frey, ML. Enhanced replication of porcine reproductive and respiratory syndrome (PRRS) virus in a homogeneous subpopulation of MA-104 cell line, Arch Virol 133:477-483, 1993.

Meng XJ., Paul PS., Halbur PG., Lum MA., Phylogenetic analyses of the putative M (ORF 6) and N (ORF 7) genes of porcine reproductive and respiratory syndrome virus (PRRSV): implication for the existence of two genotypes of PRRSV in the U.S.A. and Europe, Arch Virol 140:745-755, 1995.

Morozov I., Meng XJ., Paul PS. Sequence analysis of open reading frames (ORFs) 2 to 4 of a U.S. isolate of porcine reproductive and respiratory syndrome virus, Arch Virol 140:1313-1319, 1995.

Rossow KD., Porcine Reproductive and Respiratory Syndrome, Vet Pathol 35:1-20 (1998).

Sambrook et al., 1989, Molecular Cloning: A Laboratory Manual, 2nd ed., Cold Springs Harbor Laboratory Press, Cold Springs Harbor, NY.

Snijder EJ., Meulenberg, JJM. The molecular biology of arteriviruses, Journal of General Virology, 79:961-979, 1998.

Suárez P., Zardoya R., Martin MJ., Prieto C., Dopazo J., Solana A., Castro JM. Phytogenetic relationships of European strains of porcine reproductive and respiratory syndrome virus (PRRSV) inferred from DNA sequences of putative ORF-5 and ORF-7 genes, Virus Research 42:159-165, 1996.

Terpstra C., Wensvoort G., Pol JMA. Experimental reproduction of porcine epidemic abortion and respiratory syndrome (mystery swine disease) by infection with Lelystad virus: Koch's postulates fulfilled, The Veterinary Quarterly, vol. 13, No. 3, pp. 131-136, Jul. 1991.

Wensvoort G., Terpstra C., Pol JMA., ter Laak EA., Bloemraad M., de Kluyver EP., Kragten C., van Buiten L., den Besten A., Wagenaar F., Broekhuijsen JM., Moonen PLJM., Zetstra T., de Boer EA., Tibben HJ., de Jong MF., van't Veld P., Groenland GJR., van Gennep JA., Voets MTh., Verheijden JHM., Braamskamp J. Mystery swine disease in the Netherlands: the isolation of Lelystad virus, The Veterinary Quarterly, vol. 13, No. 3, pp. 121-130, Jul. 1991.

Zimmerman JJ., Yoon, KJ., Willis RW., Swenson SL., General overview of PRRSV: A perspective from the United States, Veterinary Microbiology 55:187-196, 1997.

Allende, R., et al., EMBL online database, AF046869, PRRS virus 16244B, complete genome, Oct. 21, 1998.

Chasin M., Domb A. "Polyanhydrides as Drug Delviery Systems" in Biodegradable Polymers as Drug Delivery Systems, vol. 45, pp. 43-70, 1990.

Den Boon, J.A. et al., 1991, J. Virol. 65(6):2910-2920.

Erlich (ed), 1992, PCR Technology, Oxford University Press, New York.

Kreutz, LC. "Cellular membrane factors are the major determinants of porcine reproductive and respiratory syndrome virus tropism," Virus Research 53:121-128, 1998.

Innis et al. (eds.), 1995, PCR Strategies, Academic Press, Inc., San Diego.

Maniatis et al., 1989, Molecular Cloning, A Laboratory Manual, Cold Sprigns Harbor Laboratory Press, Cold Springs Harbor, NY.

Meulenberg, J.J.M., Lelystad Virus, the Causative Agent or Procine Epidemic Bortion and Respiratory Syndrom (PEARS), Is Related to LDV and EAV, Virology 192, 62-72 (1993).

Murtaugh, M.P. et al., EMBL online database, U87392, PRRS virus strain VR-2332 complete genome, Jan. 8, 1998.

Nelsen, C.J., et al., GenBank, AF066183, Porcine reproductive and respiratory syndrome virus RespPRRS MLV, complete genome, May 15, 1998.

Van Dinten, L.D. et al., 1997, Proc. Natl. Acad. Sci. USA, 94(3):991-996.

Yang S X et al., Comparative sequence analysis of open reading frames 2 to 7 of the modified live vaccine virus and other North American isolates of the porcine reproductive and respiratory syndrome virus, Archives of Virology, New York, NY, US vol. 143, No. 3, 1998, pp. 601-612, XP000926565 ISSN: 0304-8608.

* cited by examiner

INFECTIOUS CDNA CLONE OF NORTH AMERICAN PORCINE REPRODUCTIVE AND RESPIRATORY SYNDROME (PRRS) VIRUS AND USES THEREOF

CROSS REFERENCE TO RELATED APPLICATION

This application is a continuation of U.S. Ser. No. 09/470,661, filed Dec. 22, 1999, now U.S. Pat. No. 6,500,662 which claims priority to U.S. Ser. No. 60/113,345, filed Dec. 22, 1998, both of which are incorporated herein by reference.

FIELD OF THE INVENTION

The present invention is in the field of animal health and is directed to infectious cDNA clones of positive polarity RNA viruses and the construction of vaccines, in particular, swine vaccines, using such cDNA clones.

BACKGROUND OF THE INVENTION

Porcine reproductive and respiratory syndrome (PRRS) is a new disease of swine, first described in 1987 in North America and in 1990 in Europe. The disease has since spread to Asia and affects most of the major swine producing countries of the world. Primary symptoms are reproductive problems in sows and gilts, including late term abortions, stillbirths and mummies, and litters of small weak pigs which are born viremic and often fail to survive. In addition, the syndrome manifests itself as a respiratory disease in young pigs which spreads horizontally and causes fever, lethargy, labored breathing, loss of appetite, slow growth, and occasionally death, often in association with other respiratory pathogens. The disease furthermore can be transmitted to sows and gilts via the semen of infected boars, either naturally or by artificial insemination. For these, and other reasons, PRRS has proven to be a difficult disease to control and therefore one of the most economically damaging diseases to the swine industry.

The causative agent of PRRS is the PRRS virus, which exists as two genetically and serologically distinct types (Murtaugh, M. P. et al., 1995, Arch-Virol. 140, 1451–1460; Suarez, P. et al., 1996, Virus Research 42:159–165). The two types are believed to have first entered swine populations independently, one in North America and the other in Europe, in the 1980's, from unknown biological reservoirs, possibly of rodent or avian origin. The European type, represented by the prototype "Lelystad Virus", was isolated and sequenced in the Netherlands in 1991 (Terpstra, C. et al., 1991, Vet. Quart. 13:131–136; Wensvoort, G. et al., 1991, Vet. Quart. 13:121–130; Wensvoort, G. et al., WO 92/213751992 (PCT/NL92/00096), 1992; Meulenberg, J. J. M. et al., 1993, Virol. 192:62–72).

Both the North American PRRS virus and the European PRRS virus are classified within the family Arteriviridae, which also includes equine arteritis virus, lactate dehydrogenase-elevating virus, and simian haemorrhagic fever virus. The arteriviruses are in turn placed within the order Nidovirales, which also includes the coronaviruses and toroviruses. The nidoviruses are enveloped viruses having genomes consisting of a single strand of positive polarity RNA. The genomic RNA of a positive-stranded RNA virus fulfills the dual role in both storage and expression of genetic information. No DNA is involved in replication or transcription in nidoviruses. The reproduction of nidoviral genomic RNA is thus a combined process of genome replication and mRNA transcription. Moreover, some proteins are translated directly from the genomic RNA of nidoviruses. The molecular biology of the family Arteriviridae has recently been reviewed by Snijder and Meulenberg (Snijder, E. J. and Meulenberg, J. J. M., 1998, Journal of General Virology 79:961–979).

Currently available commercial vaccines against PRRS are either conventional modified live virus (cell culture, attenuated) or conventional killed (inactivated cell culture preparations of virulent virus). Several of these vaccines have been criticized based on safety and/or efficacy concerns. The development of a second generation of PRRS vaccines, based upon specific additions, deletions, and other modifications to the PRRS genome, is therefore highly desirable. However, since the PRRS viruses do not include any DNA intermediates during their replication, such vaccines have thus far awaited the construction of full-length cDNA clones of PRRS viruses for manipulation by molecular biology techniques at the DNA level. Very recently, a full-length infectious cDNA clone of the European PRRS virus has been reported (Meulenberg, J. J. M. et al., 1998, supra; Meulenberg, J. J. M. et al., 1988, J. Virol. 72, 380–387.).

The preceding publications, as well as all other references discussed below in this application, are hereby incorporated by reference in their entireties.

SUMMARY OF THE INVENTION

The subject invention provides an isolated polynucleotide molecule comprising a DNA sequence encoding an infectious RNA molecule encoding a North American PRRS virus, wherein said DNA sequence is SEQ ID NO:1 or is a sequence homologous thereto.

The subject invention further provides an isolated infectious RNA molecule encoded by the isolated polynucleotide molecule recited above, and isolated infectious RNA molecules homologous thereto, which isolated infectious RNA molecules each encode a North American PRRS virus.

The subject invention further provides the above-recited isolated polynucleotide molecule encoding the infectious RNA molecule in the form of a vector such as a plasmid.

The subject invention further provides a viral vector comprising a DNA encoding an infectious RNA molecule encoding a North American PRRS virus, wherein said DNA sequence is SEQ ID NO:1 or is a DNA sequence homologous thereto.

The subject invention further provides a transfected host cell comprising a DNA sequence encoding an infectious RNA molecule encoding a North American PRRS virus, wherein said DNA sequence is SEQ ID NO:1 or is a DNA sequence homologous thereto, which transfected host cell is capable of expressing the encoded North American PRRS virus.

The subject invention further provides a method for making a genetically modified North American PRRS virus, which method comprises mutating a DNA sequence of the present invention encoding an infectious RNA molecule encoding the North American PRRS virus, and expressing the genetically modified North American PRRS virus therefrom subsequent to said mutation.

The subject invention further provides an isolated polynucleotide molecule comprising a DNA sequence encoding an infectious RNA molecule encoding a genetically modified North American PRRS virus. In a preferred embodiment, the PRRS virus is genetically modified such that when it infects a porcine animal it is: a) unable to produce PRRS in the animal, and b) able to elicit an effective immunoprotective response against infection by a PRRS virus in the animal. In a particular embodiment, the DNA sequence is SEQ ID NO:1 or a sequence homologous thereto, except for that it contains one or more mutations that genetically disable the encoded PRRS virus in its ability to produce PRRS.

The subject invention further provides an isolated infectious RNA molecule encoded by the isolated polynucleotide molecule recited above, and isolated infectious RNA molecules homologous thereto, which isolated infectious RNA molecules each encode a genetically modified North American PRRS virus, disabled in its ability to produce PRRS.

The subject invention further provides a genetically modified North American PRRS virus encoded by an infectious RNA molecule as recited above, which genetically modified North American PRRS virus is disabled such that when it infects a porcine animal it is unable to produce PRRS in the animal, yet is able to elicit an effective immunoprotective response against infection by a PRRS virus in the animal.

The subject invention further provides a viral vector comprising a DNA sequence encoding an infectious RNA molecule encoding a genetically modified North American PRRS virus as recited above.

The subject invention further provides a transfected host cell comprising a DNA sequence encoding an infectious RNA molecule encoding a genetically modified North American PRRS virus as recited above.

The subject invention further provides a vaccine for protecting a porcine animal from infection by a PRRS virus, which vaccine comprises a genetically modified North American PRRS virus as recited above; an infectious RNA molecule as recited above encoding the genetically modified North American PRRS virus; an isolated polynucleotide molecule recited above, in the form of a plasmid, encoding the genetically modified North American PRRS virus; or the above-recited viral vector encoding the genetically modified North American PRRS virus; in an amount effective to produce immunoprotection against infection by a PRRS virus; and a carrier acceptable for veterinary use.

The subject invention further provides a method for protecting a porcine animal from infection by a PRRS virus, which comprises vaccinating the animal with an amount of the above-recited vaccine that is effective to produce immunoprotection against infection by a PRRS virus.

The present invention further provides any of the aforementioned polynucleotide molecules further comprising a nucleotide sequence encoding a heterologous antigenic epitope, as well as corresponding infectious RNA molecules, vectors, transfected host cells, genetically modified North American PRRS viruses, vaccines, and methods of administering such vaccines to mammals and/or birds. Such heterologous antigenic epitopes can be from any antigenic epitope, presently known in the art, or to be determined in the future. In a non-limiting embodiment, such antigenic epitope is from a pathogen capable of pathogenically infecting a bird or mammal other than porcine animal, for example a human, and is capable of inducing an effective immunoprotective response against said pathogen. In another non-limiting embodiment, such antigenic epitope is from a swine pathogen other than a North American PRRS virus and is capable of inducing an effective immunoprotective response against said swine pathogen. In another non-limiting embodiment, such antigenic epitope is a detectable antigenic epitope.

The present invention further provides any of the aforementioned polynucleotide molecules, but which lack one or more detectable antigenic epitopes, as well as corresponding infectious RNA molecules, vectors, transfected host cells, genetically modified North American PRRS viruses, vaccines, and methods of administering such vaccines to mammals and/or birds.

The subject invention further provides an isolated polynucleotide molecule comprising one or more nucleotide sequences that encode a peptide encoded by a North American PRRS virus, wherein the genome sequence of said North American PRRS virus is SEQ ID NO:1 or a sequence homologous thereto.

The subject invention further provides a transfected host cell comprising one or more nucleotide sequences that encode a peptide encoded by a North American PRRS virus, wherein the genome sequence of said North American PRRS virus is SEQ ID NO:1 or a sequence homologous thereto.

The subject invention further provides a genetically modified Nidovirales virus that is able to elicit an effective immunoprotective response in a mammal or a bird vaccinated therewith, which genetically modified Nidovirales virus is prepared by obtaining an isolated polynucleotide molecule comprising a DNA sequence encoding an infectious RNA molecule encoding a wild-type Nidovirales virus, genetically mutating the DNA sequence so as to obtain an isolated polynucleotide molecule comprising a DNA sequence encoding an infectious RNA molecule encoding a genetically modified Nidovirales virus which virus is unable to produce a pathogenic infection yet is able to elicit an effective immunoprotective response against infection by the wild-type Nidovirales virus in a mammal or a bird, and expressing the genetically modified Nidovirales virus from the isolated polynucleotide molecule so obtained.

The subject invention further provides a method for preparing a genetically modified Nidovirales virus that is capable of eliciting an immunoprotective response in a mammal or a bird vaccinated therewith, which method comprises obtaining an isolated polynucleotide molecule comprising a DNA sequence encoding an infectious RNA molecule encoding a wild-type Nidovirales virus, genetically mutating the DNA so as to obtain an isolated polynucleotide molecule comprising a DNA sequence encoding an infectious RNA molecule encoding a genetically modified Nidovirales virus which virus is unable to produce a pathogenic infection yet able to elicit an effective immunoprotective response against infection by the wild-type Nidovirales virus in a mammal or a bird, and expressing the genetically modified Nidovirales virus from the isolated polynucleotide molecule so obtained.

The subject invention further provides a vaccine for protecting a mammal or a bird from infection by a Nidovirales virus, which vaccine comprises a genetically modified Nidovirales virus as described above in an amount effective to elicit an effective immunoprotective response against the wild-type Nidovirales virus in a mammal or a bird vaccinated therewith, and a carrier acceptable for pharmaceutical or veterinary use.

DETAILED DESCRIPTION OF THE INVENTION

Figure 1:
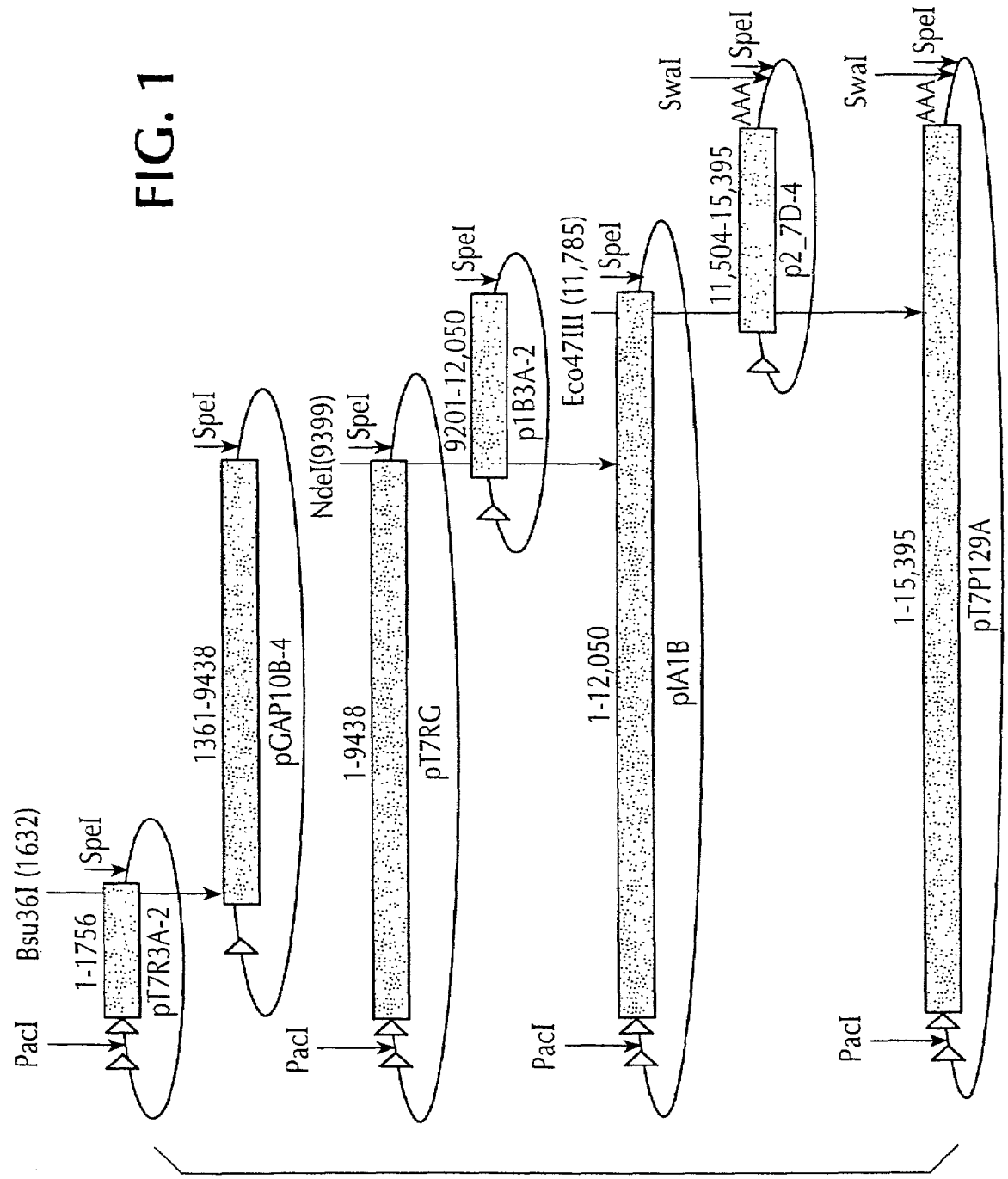
FIG. 1: Cloning strategy for construction of full-length infectious cDNA clone of North American PRRS virus, pT7P129A. Arrowheads represent T7 promoter sequences.

Production and manipulation of the isolated polynucleotide molecules described herein are within the skill in the art and can be carried out according to recombinant techniques described, among other places, in Maniatis, et al., 1989, *Molecular Cloning, A Laboratory Manual*, Cold Spring Harbor Laboratory Press, Cold Spring Harbor, N.Y.; Ausubel, et al., 1989, *Current Protocols In Molecular Biology*, Greene Publishing Associates & Wiley Interscience, NY; Sambrook, et al., 1989, *Molecular Cloning: A Laboratory Manual*, 2d ed., Cold Spring Harbor Laboratory Press, Cold Spring Harbor, N.Y.; Innis et al. (eds), 1995, *PCR Strategies*, Academic Press, Inc., San Diego; and Erlich (ed), 1992, *PCR Technology*, Oxford University Press, New York, all of which are incorporated herein by reference.

A. Isolated Polynucleotide Molecules and RNA Molecules Encoding a North American PRRS Virus, and Isolated Polynucleotide Molecules and RNA Molecules Encoding Genetically Modified North American PRRS Viruses:

The subject invention provides isolated polynucleotide molecules comprising DNA sequences that encode infectious RNA molecules that encode a North American PRRS virus. The present invention further provides isolated polynucleotide molecules comprising DNA sequences that encode infectious RNA molecules that encode genetically modified North American PRRS viruses.

In particular, the subject invention provides an isolated polynucleotide molecule comprising a DNA sequence encoding an infectious RNA molecule that encodes a North American PRRS virus, wherein said DNA sequence is SEQ ID NO:1 or a sequence homologous thereto. In a preferred embodiment, the present invention provides an isolated polynucleotide molecule comprising a DNA sequence encoding an infectious RNA molecule that encodes a North American PRRS virus, wherein said DNA sequence is the sequence beginning with and including nucleotide 1 through and including nucleotide 15,416 of SEQ ID NO:1, except that the nucleotide corresponding to nucleotide 12,622 of SEQ ID NO:1 is a guanine instead of an adenine and the nucleotide corresponding to nucleotide 1,559 of SEQ ID NO:1 is a thymine instead of a cytosine. Said DNA sequence encodes an infectious RNA molecule that is the RNA genome of the North American PRRS isolate P129.

It is understood that terms herein referring to nucleic acid molecules such as "isolated polynucleotide molecule", "nucleotide sequence", "open reading frame (ORF)", and the like, unless otherwise specified, include both DNA and RNA molecules and include both single-stranded and double-stranded molecules. Also, when reference to a particular sequence from the "Sequence Listing" section of the subject application is made, it is intended, unless otherwise specified, to refer to both the DNA of the "Sequence Listing", as well as RNA corresponding to the DNA sequence, and includes sequences complementary to the DNA and RNA sequences. In such contexts in this application, "corresponding to" refers to sequences of DNA and RNA that are identical to one another but for the fact that the RNA sequence contains uracil in place of thymine and the backbone of the RNA molecule contains ribose instead of deoxyribose.

For example, SEQ ID NO:1 is a DNA sequence corresponding to the RNA genome of a North American PRRS virus. Thus, a DNA sequence complementary to the DNA sequence set forth in SEQ ID NO:1 is a template for, i.e. is complementary to or "encodes", the RNA genome of the North American PRRS virus (i.e., RNA that encodes the North American PRRS virus). Nonetheless, a reference herein to SEQ ID NO:1 includes both the RNA sequence corresponding to SEQ ID NO:1 and a DNA sequence complementary to SEQ ID NO:1.

Furthermore, when reference is made herein to sequences homologous to a sequence in the Sequence Listing, it is to be understood that sequences homologous to a sequence corresponding to the sequence in the Sequence Listing and sequences homologous to a sequence complementary to the sequence in the Sequence Listing are also included.

An "infectious RNA molecule", for purposes of the present invention, is an RNA molecule that encodes the necessary elements for viral replication, transcription, and translation into a functional virion in a suitable host cell, provided, if necessary, with a peptide or peptides that compensate for any genetic modifications, e.g. sequence deletions, in the RNA molecule.

An "isolated infectious RNA molecule" refers to a composition of matter comprising the aforementioned infectious RNA molecule purified to any detectable degree from its naturally occurring state, if such RNA molecule does indeed occur in nature. Likewise, an "isolated polynucleotide molecule" refers to a composition of matter comprising a polynucleotide molecule of the present invention purified to any detectable degree from its naturally occurring state, if any.

For purposes of the present invention, the nucleotide sequence of a second polynucleotide molecule (either RNA or DNA) is "homologous" to the nucleotide sequence of a first polynucleotide molecule where the nucleotide sequence of the second polynucleotide molecule encodes the same polyaminoacid as the nucleotide sequence of the first polynucleotide molecule as based on the degeneracy of the genetic code, or when it encodes a polyaminoacid that is sufficiently similar to the polyaminoacid encoded by the nucleotide sequence of the first polynucleotide molecule so as to be useful in practicing the present invention. For purposes of the present invention, a polynucleotide molecule is useful in practicing the present invention where it can be used as a diagnostic probe to detect the presence of the North American PRRS virus in a fluid or tissue sample of an infected pig, e.g. by standard hybridization or amplification techniques. It is to be understood that the polyaminoacid encoded by the nucleotide sequence of the polynucleotide molecule can comprise a group of two or more polyaminoacids. Generally, the nucleotide sequence of a second polynucleotide molecule is homologous to the nucleotide sequence of a first polynucleotide molecule if it has at least about 70% nucleotide sequence identity to the nucleotide sequence of the first polynucleotide molecule as based on the BLASTN algorithm (National Center for Biotechnology Information, otherwise known as NCBI, (Bethesda, Md., USA) of the United States National Institute of Health). Preferably, a homologous nucleotide sequence has at least about 75% nucleotide sequence identity, even more preferably at least about 85% nucleotide sequence identity. Since the genetic code is degenerate, a homologous nucleotide sequence can include any number of "silent" base changes, i.e. nucleotide substitutions that nonetheless encode the same amino acid. A homologous nucleotide sequence can further contain non-silent mutations, i.e. base substitutions, deletions, or additions resulting in amino acid differences in the encoded polyaminoacid, so long as the sequence remains at least about 70% identical to the polyaminoacid encoded by the first nucleotide sequence or otherwise is useful for practicing the present invention. Homologous nucleotide sequences can be determined by comparison of nucleotide sequences, for example by using BLASTN, above. Alternatively, homologous nucleotide sequences can be determined by hybridization under selected conditions. For example, the nucleotide sequence of a second polynucleotide molecule is homologous to SEQ ID NO:1 if it hybridizes to the complement of SEQ ID NO:1 under moderately stringent conditions, e.g., hybridization to filter-bound DNA in 0.5 M NaHPO$_4$, 7% sodium dodecyl sulfate (SDS), 1 mM EDTA at 65° C., and washing in 0.2×SSC/0.1% SDS at 42° C. (see Ausubel et al. above), or conditions which will otherwise result in hybridization of sequences that encode a North American PRRS virus as defined below. In another embodiment, a second nucleotide sequence is homologous to SEQ ID NO:1 if it hybridizes to the complement of SEQ ID NO:1 under highly stringent conditions, e.g. hybridization to filter-bound DNA in 0.5 M NaHPO$_4$, 7% SDS, 1 mM EDTA at 65° C., and washing in 0.1×SSC/0.1% SDS at 68° C. (Ausubel et al., above).

It is furthermore to be understood that the isolated polynucleotide molecules and the isolated RNA molecules of the present invention include both synthetic molecules and molecules obtained through recombinant techniques, such as by in vitro cloning and transcription.

As used herein, the term "PRRS" encompasses disease symptoms in swine caused by a PRRS virus infection. Examples of such symptoms include, but are not limited to, abortion in pregnant females, and slow growth, respiratory difficulties, loss of appetite, and mortality in young pigs. As used herein, a PRRS virus that is "unable to produce PRRS" refers to a virus that can infect a pig, but which does not produce any disease symptoms normally associated with a PRRS infection in the pig, or produces such symptoms, but to a lesser degree, or produces a fewer number of such symptoms, or both.

The terms "porcine" and "swine" are used interchangeably herein and refer to any animal that is a member of the family Suidae such as, for example, a pig. "Mammals" include any warm-blooded vertebrates of the Mammalia class, including humans.

The term "PRRS virus", as used herein, unless otherwise indicated, means any strain of either the North American or European PRRS viruses.

The term "North American PRRS virus" means any PRRS virus having genetic characteristics associated with a North American PRRS virus isolate, such as, but not limited to the PRRS virus that was first isolated in the United States around the early 1990's (see, e.g., Collins, J. E., et al., 1992, *J. Vet. Diagn. Invest.* 4:117–126); North American PRRS virus isolate MN-1 b (Kwang, J. et al., 1994, *J. Vet. Diagn. Invest* 6:293–296); the Quebec IAF-exp91 strain of PRRS (Mardassi, H. et al., 1995, *Arch. Virol.* 140:1405–1418); and North American PRRS virus isolate VR 2385 (Meng, X.-J et al., 1994, *J. Gen. Virol.* 75:1795–1801). Genetic characteristics refers to genomic nucleotide sequence similarity and aminoacid sequence similarity shared by North American PRRS virus strains. For purposes of the present invention, a North American PRRS virus is a virus that is encoded by an RNA sequence the same as or homologous to SEQ ID NO:1, wherein the term "homologous" is as defined previously. Thus, strains of North American PRRS viruses have, preferably, at least about 70% genomic nucleotide sequence identity with SEQ ID NO:1, and more preferably at least about 75% genomic nucleotide sequence identity with SEQ ID NO:1, at least about 85% genomic nucleotide sequence identity with SEQ ID NO:1 being even more preferred.

The term "European PRRS virus" refers to any strain of PRRS virus having the genetic characteristics associated with the PRRS virus that was first isolated in Europe around 1991 (see, e.g., Wensvoort, G., et al., 1991, Vet. Q. 13:121–130). "European PRRS virus" is also sometimes referred to in the art as "Lelystad virus".

Unless otherwise indicated, a North American PRRS virus is "useful in practicing the present invention" if its characteristics are within the definition of a North American PRRS virus set forth herein. For example, a virus encoded by one of the isolated polynucleotide molecules of the present invention is a "North American PRRS virus useful in practicing the present invention" if it, e.g., has genetic characteristics associated with a North American PRRS virus.

Other polyaminoacids are "useful in practicing the present invention", e.g., peptides encoded by polynucleotide sequences homologous to North American PRRS virus ORFs, if they can compensate for an RNA molecule encoding a genetically modified PRRS virus, deficient in a gene essential for expressing functional PRRS virions, in a transfected host cell so that functional PRRS virions can be generated by the cell.

The term "open reading frame", or "ORF", as used herein, means the minimal nucleotide sequence required to encode a particular PRRS virus protein without an intervening stop codon.

Terms such as "suitable host cell" and "appropriate host cell", unless otherwise indicated, refer to cells into which RNA molecules (or isolated polynucleotide molecules or viral vectors comprising DNA sequences encoding such RNA molecules) of the present invention can be transformed or transfected. "Suitable host cells" for transfection with such RNA molecules, isolated polynucleotide molecules, or viral vectors, include mammalian, particularly porcine, and avian cells, and are described in further detail below.

A "functional virion" is a virus particle that is able to enter a cell capable of hosting a PRRS virus, and express genes of its particular RNA genome (either an unmodified genome or a genetically modified genome as described herein) within the cell. Cells capable of hosting a PRRS virus include porcine alveolar macrophage cells and MARC 145 monkey kidney cells. Other mammalian or avian cells, especially other porcine cells, may also serve as suitable host cells for PRRS virions.

The isolated polynucleotide molecules of the present invention encode North American PRRS viruses that can be used to prepare live, killed, or attenuated vaccines using art-recognized methods for protecting swine from infection by a PRRS virus, as described in further detail below. These isolated polynucleotide molecules are also useful as vectors for delivering heterologous genes into mammals, including swine, or birds, as is also described in detail below. Furthermore, these isolated polynucleotide molecules are useful because they can be mutated using molecular biology techniques to encode genetically-modified North American PRRS viruses useful, inter alia, as vaccines for protecting swine from PRRS infection. Such genetically-modified North American PRRS viruses, as well as vaccines comprising them, are also described in further detail below.

Accordingly, the subject invention further provides a method for making a genetically modified North American PRRS virus, which method comprises mutating the DNA sequence encoding an infectious RNA molecule which encodes the North American PRRS virus as described above, and expressing the genetically modified North American PRRS virus using a suitable expression system. A North American PRRS virus, either wild-type or genetically modified, can be expressed from an isolated polynucleotide molecule using suitable expression systems generally known in the art, examples of which are described in this application. For example, the isolated polynucleotide molecule can be in the form of a plasmid capable of expressing the encoded virus in a suitable host cell in vitro, as is described in further detail below.

The term "genetically modified", as used herein and unless otherwise indicated, means genetically mutated, i.e. having one or more nucleotides replaced, deleted and/or added. Polynucleotide molecules can be genetically mutated using recombinant techniques known to those of ordinary skill in the art, including by site-directed mutagenesis, or by random mutagenesis such as by exposure to chemical mutagens or to radiation, as known in the art. In one embodiment, genetic modification of the North American PRRS virus of the present invention renders the virus unable to replicate effectively, or reduces its ability to replicate effectively, in a bird or mammal in which the wild-type virus otherwise can effectively replicate. In another embodiment, the genetically modified North American PRRS virus of the present invention remains able to replicate effectively in birds or mammals infected therewith. "Effective replication" means the ability to multiply and produce progeny viruses (virions) in an infected animal, i.e. the ability to "productively infect" an animal.

The subject invention further provides an isolated polynucleotide molecule comprising a DNA sequence encoding an infectious RNA molecule which encodes a genetically modified North American PRRS virus that is unable to produce PRRS in a porcine animal, wherein the Ad DNA sequence encoding the infectious RNA molecule encoding said North American PRRS virus is SEQ ID NO:1 or a sequence homologous thereto, except that it contains one or more mutations that genetically disable the encoded PRRS virus in its ability to produce PRRS. "Genetically disabled" means that the PRRS virus is unable to produce PRRS in a swine animal infected therewith.

In one embodiment, the genetically modified North American PRRS virus disabled in its ability to cause PRRS is able to elicit an effective immunoprotective response against infection by a PRRS virus in a swine animal. Accordingly, the subject invention also provides an isolated polynucleotide molecule comprising a DNA sequence encoding an infectious RNA molecule which encodes a North American PRRS virus that is genetically modified such that when it infects a porcine animal it: a) is unable to produce PRRS in the animal, and b) is able to elicit an effective immunoprotective response against infection by a PRRS virus in the animal, wherein the DNA sequence encoding said North American PRRS virus is SEQ ID NO:1 or a sequence homologous thereto, except that it contains one or more mutations that genetically disable the encoded PRRS virus in its ability to produce PRRS.

The term "immune response" for purposes of this invention means the production of antibodies and/or cells (such as T lymphocytes) that are directed against, or assist in the decomposition or inhibition of, a particular antigenic epitope or particular antigenic epitopes. The phrases "an effective immunoprotective response", "immunoprotection", and like terms, for purposes of the present invention, mean an immune response that is directed against one or more antigenic epitopes of a pathogen so as to protect against infection by the pathogen in a vaccinated animal. For purposes of the present invention, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

An "antigenic epitope" is, unless otherwise indicated, a molecule that is able to elicit an immune response in a particular animal or species. Antigenic epitopes are proteinaceous molecules, i.e. polyaminoacid sequences, optionally comprising non-protein groups such as carbohydrate moieties and/or lipid moieties.

The term "pathogenically infecting" used herein refers to the ability of a pathogen to infect an animal and cause a disease in the animal. As an example, a PRRS virus is capable of pathogenically infecting a porcine animal since it can cause PRRS in swine. However, although a PRRS virus may be able to infect, either productively or non-productively, a bird or another mammal, such as a human, it does not pathogenically infect any animal other than a porcine animal since it does not cause any disease in animals other than porcine animals.

The genetically modified North American PRRS viruses encoded by the above-described isolated polynucleotide molecules are, in one embodiment, able to elicit an effective immunoprotective response against infection by a PRRS virus. Such genetically modified North American PRRS viruses are preferably able to elicit an effective immunoprotective response against any strain of PRRS viruses, including both European and North American strains.

In one embodiment, the mutation or mutations in the isolated polynucleotide molecule encoding the genetically disabled North American PRRS virus are non-silent and occur in one or more open reading frames of the nucleotide sequence encoding the North American PRRS virus; i.e., the mutation or mutations occur in one or more of the sequences within the nucleotide sequence encoding the North American PRRS virus that are the same as or homologous to ORFs 1a, 1b, 2, 3, 4, 5, 6, or 7 of SEQ ID NO:1. In another embodiment, the mutation or mutations occur in one or more noncoding regions of the North American PRRS virus genome, such as, for example, in the leader sequence of the North American PRRS virus genome; i.e., the mutation or mutations occur within the sequence that is the same as or homologous to the sequence of nucleotides 1–191 of SEQ ID NO:1. In the same isolated polynucleotide molecule, mutations can occur in both coding and noncoding regions.

As used herein, unless otherwise indicated, "noncoding regions" of the nucleotide sequence encoding the North American PRRS virus refer to those sequences of RNA that are not translated into a protein and those sequences of cDNA that encode such RNA sequences. Coding regions refer to those sequences of RNA from which North American PRRS virus proteins are expressed, and also refer to cDNA that encodes such RNA sequences. Likewise, "ORFs" refer both to RNA sequences that encode North American PRRS virus proteins and to cDNA sequence encoding such RNA sequences.

Determining suitable locations for a mutation or mutations that will encode a North American PRRS virus that is genetically disabled so that it is unable to produce PRRS yet remains able to elicit an effective immunoprotective response against infection by a PRRS virus can be made based on the SEQ ID NO:1 provided herein. One of ordinary skill can refer to the sequence of the infectious cDNA clone of North American PRRS virus provided by this invention, make sequence changes which will result in a mutation, and test the viruses encoded thereby both for their ability to produce PRRS in swine, and to elicit an effective immunoprotective response against infection by a PRRS virus. In so doing, one of ordinary skill can refer to techniques known in the art and also those described and/or exemplified herein.

For example, an ORF of the sequence encoding the infectious RNA molecule encoding the North American PRRS virus can be mutated and the resulting genetically modified North American PRRS virus tested for its ability to cause PRRS. The ORF of a North American PRRS virus encodes proteins as follows: ORF 1a encodes a polyprotein comprising protease function; ORF 1b encodes a polyprotein comprising replicase (RNA polymerase) and helicase functions; ORFs 2, 3, and 4 encode small membrane glycoproteins; ORF 5 encodes a major envelope glycoprotein; ORF 6 encodes a nonglycosylated integral membrane protein; and ORF 7 encodes a nucleocapsid protein. Genetic mutations of one or more of these ORFs can be used in preparing the genetically modified North American PRRS viruses described infra.

The subject invention also provides an isolated polynucleotide molecule comprising a DNA sequence encoding an infectious RNA molecule encoding a North American PRRS virus that is genetically modified such that it comprises one or more heterologous antigenic epitopes, wherein the DNA sequence encoding the RNA molecule encoding the North American PRRS virus is SEQ ID NO:1 or a sequence homologous thereto, and further comprising one or more additional nucleotide sequences that each encode a heterologous antigenic epitope, and wherein each heterologous antigenic epitope is capable of inducing an effective immunoprotective response against a particular pathogen in a mammal or a bird.

A pathogen against which an effective immunoprotective response can be induced by means of the above recited aspect of the present invention is any pathogen, such as a virus, bacteria, fungus, or protozoan, capable of causing a disease in a mammal or bird, which pathogen comprises or has associated therewith one or more antigenic epitopes which can be used to induce an effective immunoprotective response against the pathogen in the mammal or bird.

The term "heterologous antigenic epitope" for purposes of the present invention means an antigenic epitope, as defined above, not normally found in a wild-type North American PRRS virus. A nucleotide sequence encoding a heterologous antigenic epitope can be inserted into a North American PRRS viral genome using known recombinant techniques. Antigenic epitopes useful as heterologous antigenic epitopes for the present invention include additional North American PRRS virus antigenic epitopes, antigenic epitopes from European PRRS viruses, antigenic epitopes from swine pathogens other than PRRS viruses, or antigenic epitopes from pathogens that pathogenically infect birds or mammals other than swine, including humans. Sequences encoding such antigenic epitopes are known in the art or are provided herein. For example, a second North American PRRS virus envelope protein, encoded by North American PRRS ORF 5 described herein, can be inserted into a DNA sequence encoding an RNA molecule encoding a North American PRRS virus of the present invention to generate a genetically modified North American PRRS virus comprising an additional envelope protein as a heterologous antigenic epitope. Such a genetically modified North American PRRS virus can be used to induce a more effective immunoprotective response against PRRS viruses in a porcine animal vaccinated therewith.

Examples of an antigenic epitope from a swine pathogen other than a North American PRRS virus include, but are not limited to, an antigenic epitope from a swine pathogen selected from the group consisting of European PRRS, porcine parvovirus, porcine circovirus, a porcine rotavirus, swine influenza, pseudorabies virus, transmissible gastroenteritis virus, porcine respiratory coronavirus, classical swine fever virus, African swine fever virus, encephalomyocarditis virus, porcine paramyxovirus, *Actinobacillus pleuropneumoni, Bacillus anthraci, Bordetella bronchiseptica, Clostridium haemolyticum, Clostridium perfringens, Clostridium tetani, Escherichia coli, Erysipelothrix rhusiopathiae, Haemophilus parasuis, Leptospira* spp., *Mycoplasma hyopneumoniae, Mycoplasma hyorhinis, Pasteurella haemolytica, Pasteurella multocida, Salmonella choleraesuis, Salmonella typhimurium, Streptococcus equismilis*, and *Streptococcus suis*. Nucleotide sequences encoding antigenic epitopes from the aforementioned swine pathogens are known in the art and can be obtained from public gene databases such as GenBank (http://www.ncbi.nim.nih.gov/Web/Genbank/index.html) provided by NCBI.

If the heterologous antigenic epitopes are antigenic epitopes from one or more other swine pathogens, then the isolated polynucleotide molecule can further contain one or more mutations that genetically disable the encoded PRRS virus in its ability to produce PRRS. Such isolated polynucleotide molecules and the viruses they encode are useful for preparing vaccines for protecting swine against the swine pathogen or pathogens from which the heterologous antigenic epitopes are derived.

In a preferred embodiment, the genetically modified North American PRRS is able to elicit an effective immunoprotective response against infection by a PRRS virus in a porcine animal. Such isolated polynucleotide molecules and the viruses they encode are useful for preparing dual-function vaccines for protecting swine against infection by both a North American PRRS virus and the swine pathogen or pathogens from which the heterologous antigenic epitopes are derived. In another preferred embodiment, the genetically modified North American PRRS virus useful in a dual-function vaccine is genetically disabled.

The isolated polynucleotide molecules of the present invention comprising nucleotide sequences encoding heterologous antigenic epitopes can be prepared as described above based on the sequence encoding a North American PRRS virus described herein using known techniques in molecular biology.

In a further preferred embodiment, a heterologous antigenic epitope of the genetically modified North American PRRS virus of the present invention is a detectable antigenic epitope. Such isolated polynucleotide molecules and the North American PRRS viruses they encode are useful, inter alia, for studying PRRS infections in swine, determining successfully vaccinated swine, and/or for distinguishing vaccinated swine from swine infected by a wild-type PRRS virus. Preferably, such isolated polynucleotide molecules further contain one or more mutations that genetically disable the encoded PRRS virus in its ability to produce PRRS, and more preferably are able to elicit an effective immunoprotective response in a porcine animal against infection by a PRRS virus.

Heterologous antigenic epitopes that are detectable, and the sequences that encode them, are known in the art. Techniques for detecting such antigenic epitopes are also known in the art and include serological detection of antibody specific to the heterologous antigenic epitope by means of, for example, Western blot, ELISA, or fluorescently labeled antibodies capable of binding to the antibodies specific to the heterologous antigenic epitope. Techniques for serological detection useful in practicing the present invention can be found in texts recognized in the art, such as Coligan, J. E., et al. (eds), 1998, *Current Protocols in Immunology*, John Willey & Sons, Inc., which is hereby incorporated by reference in its entirety. Alternatively, the heterologous antigenic epitope itself can be detected by, for example, contacting samples that potentially comprise the antigenic epitope with fluorescently-labeled antibodies or radioactively-labeled antibodies that specifically bind to the antigenic epitopes.

The present invention further provides an isolated polynucleotide molecule comprising a DNA sequence encoding an infectious RNA molecule which encodes a genetically modified North American PRRS virus that detectably lacks a North American PRRS virus antigenic epitope, wherein the DNA sequence encoding the RNA molecule encoding the North American PRRS virus is SEQ ID NO:1 or a sequence homologous thereto, except that it lacks one or more nucleotide sequences encoding a detectable North American PRRS virus antigenic epitope. Such isolated polynucleotide molecules are useful for distinguishing between swine infected with a recombinant North American PRRS virus of the present invention and swine infected with a wild-type PRRS virus. For example, animals vaccinated with killed, live or attenuated North American PRRS virus encoded by such an isolated polynucleotide molecule can be distinguished from animals infected with wild-type PRRS based on the absence of antibodies specific to the missing antigenic epitope, or based on the absence of the antigenic epitope itself: If antibodies specific to the missing antigenic epitope, or if the antigenic epitope itself, are detected in the animal, then the animal was exposed to and infected by a wild-type PRRS virus. Means for detecting antigenic epitopes and antibodies specific thereto are known in the art, as discussed above. Preferably, such an isolated polynucleotide molecule further contains one or more mutations that genetically disable the encoded PRRS virus in its ability to produce PRRS. More preferably, the encoded virus remains able to elicit an effective immunoprotective response against infection by a PRRS virus.

B. Plasmids Encoding a North American PRRS Virus or a Genetically Modified North American PRRS Virus:

The present invention also provides any of the above-described isolated polynucleotide molecules in the form of a plasmid capable of expressing the North American PRRS virus encoded thereby.

Plasmids of the present invention can express the encoded North American PRRS virus outside of a living organism, to produce North American PRRS viruses of the invention useful, inter alia, for preparing vaccines. In one embodiment, a plasmid of the present invention capable of expressing a North American PRRS virus outside of a living organism is a plasmid wherein transcription of viral RNA therefrom occurs in vitro (i.e. extracellularly); the resulting viral RNA molecule is transfected into a suitable host cell using known mechanisms of transfection, such as electroporation, lipofection (in some cases using a commercially available reagent, such as Lipofectin™ (Life Technologies Inc., Rockville, Md., USA)), or DEAE dextran mediated transfection. Other methods of transfection are known in the art and can be employed in the present invention. An example of such a plasmid for in vitro transcription of North American PRRS viral RNA is the plasmid pT7P129A (ATCC Accession No. 203488). Any promoter useful for in vitro transcription can be used in such plasmids of this invention. T7 is one such promoter, but other promoters can be used, such as an SP6 promoter or a T3 promoter. The sequences of such promoters can be artificially synthesized or cloned from commercially available plasmids. Suitable plasmids for preparing such plasmids capable of expressing North American PRRS virus include, but are not limited to, general purpose cloning vector plasmids such as pCR2.1 (Invitrogen, Carlsbad, Calif., USA), pBR322, and pUC18. A nucleotide sequence of the present invention encoding the North American PRRS virus can be inserted into any of these plasmids using known recombinant techniques. Other plasmids into which the polynucleotide molecules of the present invention can be inserted will be recognized by those of ordinary skill in the art.

Suitable conditions for in vitro transcription of viral RNA from any of the above-described recombinant plasmids comprising a DNA sequence encoding an infectious RNA molecule encoding a North American PRRS virus depends on the type of plasmid, for example, its particular promoter, and can be ascertained by one of ordinary skill in the art. For example, if a plasmid of the present invention is based on a pCR2.1 plasmid comprising a T7 promoter, then an example of suitable conditions for in vitro transcription includes reacting the plasmid with T7 RNA polymerase and ribonucleotides in a standard buffer and incubating the reaction at 37° C. for about 30 minutes. In some cases, commercial kits are available for transcribing RNA from a particular plasmid, and such kits can be used in the present invention. The reaction mixture following transcription can be directly transfected into a suitable host cell without purification, or the transcribed North American PRRS virus RNA can be purified by known RNA purification techniques, for example by organic (e.g. phenol) extraction and alcohol (e.g. ethanol or isopropanol) precipitation, prior to transfection.

Practically any mammalian or avian cell culture can be transfected with the North American PRRS virus RNA obtained as described above in order to generate a first round of North American PRRS virions. An example of cells which one might find particularly useful because of their ready availability and ease of use are BHK (baby hamster kidney) cells. However, if one wishes to generate a cell culture capable of sustained production of North American PRRS virions, then porcine alveolar macrophage cells or MARC-145 cells (Kim, H. S., et al., supra) are preferred since these cells excrete high levels of new generation PRRS virions subsequent to PRRS virus infection. Other cell lines derived from the MA-104 cell line may also be used for sustained generation of North American PRRS virions of the present invention. Primary porcine alveolar macrophage cells can be obtained by lung lavages from pigs, and the MARC-145 monkey kidney cell line can be obtained from the National Veterinary Services Laboratories otherwise known as NVSL (Ames, Iowa, USA).

In another embodiment, a plasmid capable of expressing a North American PRRS virus of the present invention outside of a living organism is a plasmid which is transfected into a suitable host cell, for example by electroporation or lipofection, transcription of the infectious RNA molecule and expression of the North American PRRS virus therefrom occurring within the transfected host cell. The transfected host cell therefore generates North American PRRS virions. Such a completely cellular method has heretofore never been disclosed or suggested for any virus within the order of Nidovirales. Because of possible cryptic splicing and termination sequences present in the RNA genome of viruses of the Nidovirales order, a completely cellular method of expressing a Nidovirales virus was believed unlikely. Cryptic sequences include RNA splice donor and splice acceptor sequences, which could cause inappropriate splicing of the RNA transcript, as well as polyadenylation sequences, which could cause premature termination by the cellular RNA polymerase II. The present invention demonstrates, however, that the presence of such sequences in a plasmid comprising a cDNA clone of a Nidovirus does not prevent the plasmid's ability to express the Nidovirus when the plasmid is directly transfected into a suitable host cell.

Accordingly, the subject invention also provides plasmids and a completely cellular method for expressing a Nidovirales virus, wherein the plasmid comprises: a) a DNA sequence encoding an infectious RNA molecule encoding the Nidovirales virus; and b) a promoter capable of transcribing said encoding sequence in a cell, wherein said promoter is in operative association with the DNA sequence encoding the infectious RNA molecule. The method comprises transfecting a suitable host cell with such a plasmid, subjecting the transfected host cell to conditions suitable for expression of gene sequences transfected therein, and collecting the expressed Nidovirales virus therefrom. An example of a plasmid suitable for completely cellular expression of North American PRRS virus outside of a living organism is the plasmid pCMV-S-P129 (ATCC Accession No. 203489). In a preferred embodiment, the promoter of such a plasmid is a CMV promoter. In a preferred embodiment, a plasmid of the invention suitable for a completely cellular method of expressing a Nidovirales virus comprises a eukaryotic promoter, such as a CMV promoter, immediately upstream and adjacent to the nucleotide sequence encoding the Nidovirales virus. In a preferred embodiment, the nucleotide sequence encoding the Nidovirales virus encodes a PRRS virus, either European or North American. Other examples of Nidovirales viruses that can be expressed by means of the above-described completely cellular method include other Arteriviruses such as, equine arteritis virus, lactate dehydrogenase-elevating virus, and simian haemorrhagic fever virus; viruses that are members of the genus *Coronaviridae*, such as, but not limited to, feline infectious peritinitis virus, feline enteric coronavirus, canine coronavirus, bovine coronavirus, porcine respiratory coronavirus, turkey coronavirus, porcine transmissible gastroenteritis virus, human coronavirus, murine hepatitis virus, and avian infectious bronchitis virus; and members of the genus *Toroviridae*, such as, but not limited to, Berne virus, Breda virus, and human torovirus. Thus, plasmids suitable for completely cellular expression comprising a nucleotide sequence encoding one of these viruses are also encompassed by the present invention.

Suitable plasmids that can be used to prepare recombinant plasmids of the present invention for completely cellular expression outside of a living organism of a Nidovirales virus, such as a PRRS virus, include virtually any plasmid useful for transfection and expression in eukaryotic cells. An examples of a plasmid suitable for preparing recombinant plasmids of the present invention for completely cellular expression of a Nidovirales virus is the plasmid pCMVbeta (Clontech, Palo Alto, Calif., USA). Other plasmids which are able to transfect and express genes in eukaryotic cells which can be used to prepare plasmids of the present invention include, but are not limited to, pcDNA3.1, pRc/RSV, and pZeoSV2 (all from Invitrogen); and pCMV-Sport3 and pSV-Sport1 (both from Life Technologies Inc.). However, almost any eukaryotic expression vector will work for the present invention. Constructs based on cosmids can also be used for completely cellular ex vivo expression of a Nidovirales virus.

Suitable host cells for the completely cellular method of the present invention for expressing PRRS virus include porcine alveolar macrophage cells and the MARC-145 cells, described above. Methods of transfecting these cells with a plasmid are basically the same as those methods for transfecting cells with viral RNA described above. Such methods include, but are not limited to, electroporation, lipofection, DEAE dextran mediated transfection, and calcium phosphate coprecipitation.

Once host cells, such as porcine alveolar macrophage cells or a MARC-145 cells, have been transfected according to the subject invention, either with viral RNA or with a plasmid comprising a nucleotide sequence encoding a virus, then the cells can be frozen at about −80° C. or below for storage for up to several years. For longer periods of time, i.e. decades, storage in liquid nitrogen is preferred. If relatively frequent use of the encoded virus is envisioned, then cells hosting the virus can also be maintained (unfrozen) in culture using known techniques, for shorter periods of time. Moreover, viral particles excreted by such cells can be stored frozen at about −80° C. or below as a source of virus. Transfection of such cell lines with the polynucleotide molecule encoding the virus can be confirmed if desired, for example, by testing exhausted medium excreted by the cell line for a PRRS virus antigen using an immunofluorescent antibody test. Antibodies which are specific for PRRS virus antigens are known in the art (see, e.g., Collins, E. J., et al., WO 93/03760 Mar. 4, 1993).

In another embodiment, a plasmid of the present invention comprising a nucleotide sequence encoding a North American PRRS virus is suitable for in vivo expression of the North American PRRS virus, i.e. expression in a living organism. Plasmids which can be used for preparing recombinant plasmids for in vivo expression of a North American PRRS virus include, but are not limited to the plasmids capable of transfecting eukaryotic cells described above, such as pCMVbeta.

Animals that can be transfected with plasmids of the present invention include mammals and birds. If the animal is other than a porcine animal, for example, a mallard duck, then the plasmid can comprise a nucleotide sequence encoding a North American PRRS virus comprising further antigenic epitopes from pathogens which are capable of pathogenically infecting the animal; in such a case, the plasmid will encode a North American PRRS virus serving as a vector for transporting epitopes into the animal. If the animal is a porcine animal, then the plasmid can usefully encode any of the North American PRRS viruses described herein, including the genetically-modified North American PRRS viruses described herein.

C. Viral Vectors Encoding a North American PRRS Virus, Including Viral Vectors Encoding Genetically Modified North American PRRS Viruses:

The present invention also provides viral vectors comprising a DNA sequence encoding an infectious RNA molecule encoding any of the North American PRRS viruses described herein, including the genetically-modified North American PRRS viruses described herein. Such viral vectors are useful for transfecting eukaryotic cells for production of PRRS viruses of the present invention outside of a living organism, or for transfecting swine, or other mammals, or avians, with the sequence encoding the North American PRRS virus, for in vivo expression of the North American PRRS virus therein.

Some examples of viruses that can be used as vectors for preparing the viral vectors of the present invention include, but are not limited to, swine viruses such as, but not limited to, swine pox virus, pseudorabies virus, or African swine fever virus. Such swine viruses can be obtained from The National Veterinary Services Laboratories (Ames, Iowa, USA) of the United States Department of Agriculture; the American Type Culture Collection, otherwise known as the ATCC (Manassas, Va., USA); and other known sources. Recombinant viral vectors based on suitable swine viruses such as the aforementioned swine viruses are useful for transfecting swine animals with a nucleotide sequence encoding a North American PRRS virus of the present invention.

Viral vectors comprising a DNA sequence encoding an infectious RNA molecule encoding a North American PRRS virus of the present invention based on these and other viruses can be prepared using known recombinant techniques described in texts such as those cited previously in this application.

D. Transfected Host cells Encoding or a Genetically Modified North American PRRS Viruses:

The present invention also provides transfected host cells that comprise a DNA sequence encoding an infectious RNA molecule encoding any of the North American PRRS viruses described herein, including the genetically-modified North American PRRS viruses described herein, which transfected host cells are capable of expressing the North American PRRS virus. Such transfected host cells are useful for producing North American PRRS viruses of the present invention. Examples of transfected host cells of the present invention include the transfected porcine alveolar macrophage cells and the transfected MARC-145 cells described above.

Other transfected host cells of the invention include, but are not limited to, transfected MA-104 cells and other derivatives of MA-104 cells that are transfected; transfected Baby Hamster Kidney (BHK) cells; transfected Chinese Hamster Ovary (CHO) cells; and African Green Monkey kidney cells other than MA-104 cells or MARC-145 cells, such as VERO cells; that are transfected.

E. North American PRRS Viruses, Including Genetically Modified North American PRRS Viruses:

The present invention also provides North American PRRS viruses as described herein, including genetically-modified North American PRRS viruses as described herein, expressed and/or encoded by any of the above-described isolated polynucleotide molecules, RNA molecules, plasmids, viral vectors, or transfected host cells.

In certain situations, for example where the North American PRRS virus is to be used in a vaccine for swine and the North American PRRS virus has not been genetically modified as described above so as to be unable to cause PRRS, it is desirable to treat the North American PRRS virus, for example by inactivating or attenuating it, so that it is unable to cause PRRS in swine to which it is administered. Known methods can be used to inactivate a North American PRRS virus of the present invention so that it is unable to cause PRRS in an animal. Examples of such methods include, but are not limited to, treatment with formaldehyde, BEI (binary ethyleneimine), or BPL (beta-propiolactone). Methods of attenuation are also known in the art, and such methods can be used to attenuate a North American PRRS virus of the present invention. A North American PRRS virus of the present invention can, for example, be attenuated by serial passage in cell culture.

If a North American PRRS virus of the present invention is for use in an animal other than a porcine animal, or if it has been genetically modified as described herein so that it is unable to produce PRRS in a porcine animal, then it is not necessary to treat the virus as described in the preceding paragraph prior to using it in a vaccine.

F. Vaccines and Uses Thereof:

The present invention also provides vaccines comprising North American PRRS viruses, including genetically modified North American PRRS viruses disabled in their ability to produce PRRS in a swine animal as described herein; infectious RNA molecules and plasmids encoding such North American PRRS viruses as described herein; and viral vectors encoding such North American PRRS viruses and isolated RNA molecules as described herein. The invention also provides methods for protecting animals from infection comprising vaccination with such vaccines.

In a preferred embodiment, the subject invention provides a vaccine comprising a genetically modified North American PRRS virus comprising one or more heterologous antigenic epitopes as described herein, an infectious RNA molecule encoding such a genetically modified North American PRRS virus, or a plasmid as described herein encoding such a genetically modified North American PRRS virus, in an amount effective to elicit an immunoprotective response against infection by the pathogen or pathogens from which the a heterologous antigenic epitope(s) are derived, and a carrier acceptable for pharmaceutical or veterinary use.

Such vaccines can be used to protect from infection a mammal or a bird capable of being pathogenically infected by the pathogen or pathogens from which the heterologous antigenic epitope(s) are derived. Accordingly, the subject invention also provides a method for protecting a mammal or a bird from infection by a pathogen, which comprises vaccinating the mammal or bird with an amount of the vaccine described in the preceding paragraph effective to elicit an immunoprotective response in the mammal or bird from infection by the pathogen.

In a further preferred embodiment, the vaccine comprises a genetically modified North American PRRS virus, or an infectious RNA molecule or plasmid encoding such a genetically modified North American PRRS virus, comprising or encoding one or more heterologous antigenic epitopes from a swine pathogen other than a North American PRRS virus These vaccines are useful for protecting swine from infection by the swine pathogen or pathogens from which the heterologous antigenic epitope(s) are derived. If such a vaccine comprises the genetically modified North American PRRS virus, the genetic modification of the North American PRRS virus preferably preferably renders the virus unable to cause PRRS in swine. In another preferred embodiment, the genetically modified North American PRRS virus in the vaccine is able to elicit an immunoprotective response against infection by a PRRS virus, thus providing a dual-vaccine for swine, protecting swine from infection by the swine pathogen or pathogens from which the heterologous antigenic epitope(s) are derived as well as from infection by a PRRS virus. If the vaccine comprises an infectious RNA molecule or a plasmid encoding a genetically-modified North American PRRS virus comprising one or more heterologous antigenic epitopes from another swine pathogen, then the sequence encoding the infectious RNA molecule encoding the genetically modified PRRS virus preferably comprises one or more further mutations that genetically disable the encoded North American PRRS virus so that it is unable to cause PRRS. In another preferred embodiment, the encoded genetically modified, disabled North American PRRS virus is able to elicit an immunoprotective response against a PRRS infection in a swine animal, thus providing a dual-vaccine for swine, able to protect swine from infection by the swine pathogen or pathogens from which the heterologous antigenic epitope(s) are derived as well as from infection by a PRRS virus. All of these vaccines also further comprise a carrier acceptable for veterinary use.

The present invention further provides a method for protecting a porcine animal from infection by a swine pathogen or pathogens other than a North American PRRS virus and, optionally, for simultaneously protecting the swine animal from infection by a PRRS virus, which comprises vaccinating the animal with an amount of a vaccine described in the preceding paragraph effective to elicit an immunoprotective response in the swine animal from an infection by the swine pathogen or pathogens and optionally, by a PRRS virus.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's *Pharmaceutical Science*, 18th ed., 1990, Mack Publishing, which is incorporated herein by reference.

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol. Other immunomodulatory agents that can be included in the vaccine include, e.g., one or more interleukins, interferons, or other known cytokines.

Vaccines of the present invention can optionally be formulated for sustained release of the virus, infectious RNA molecule, plasmid, or viral vector of the present invention. Examples of such sustained release formulations include virus, infectious RNA molecule, plasmid, or viral vector in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279–292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: *Drugs and the Pharmaceutical Sciences*, Vol. 45, M. Dekker, NY, which is also incorporated herein by reference. Alternatively, or additionally, the virus, plasmid, or viral vector can be microencapsulated to improve administration and efficacy. Methods for microencapsulating antigens are well-known in the art, and include techniques described, e.g., in U.S. Pat. No. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Patent Publication WO 95/28227, all of which are incorporated herein by reference.

Liposomes can also be used to provide for the sustained release of virus, plasmid, or viral vector. Details concerning how to make and use liposomal formulations can be found in, among other places, U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

An effective amount of any of the above-described vaccines can be determined by conventional means, starting with a low dose of virus, plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, infectious RNA molecule, plasmid, or viral vector, of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present invention in a vaccine of the present invention preferably ranges from about 0.1 µg to about 100 mg, more preferably from about 1 µg to about 10 mg, even more preferably from about 10 µg to about 1 mg. The dose amount of an infectious RNA molecule of the present invention in a vaccine of the present invention preferably ranges from about 0.1 µg to about 100 mg, more preferably from about 1 µg to about 10 mg, even more preferably from about 10 µg to about 1 mg. The dose amount of a viral vector of the present invention in a vaccine of the present invention preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

The present invention further provides a method of preparing a vaccine comprising a North American PRRS virus, infectious RNA molecule, plasmid, or viral vector described herein, which method comprises combining an effective amount of one of the North American PRRS virus, infectious RNA molecule, plasmid, or viral vector of the present invention, with a carrier acceptable for pharmaceutical or veterinary use.

It is to be understood that the term "North American PRRS viruses of the present invention" and like terms, unless otherwise indicated, include any of the genetically modified North American PRRS viruses described herein as well as the unmodified North American PRRS virus described herein encoded by SEQ ID NO:1 or a sequence homologous thereto.

G. Isolated Polynucleotide Molecules and Transfected Host cells Encoding North American PRRS Virus Peptides, and Methods for Making Functional North American PRRS Virions:

The present invention also provides an isolated polynucleotide molecule comprising one or more nucleotide sequences that encode a peptide encoded by a North American PRRS virus, wherein the genome sequence of said North American PRRS virus is the same as or homologous to an RNA molecule corresponding to SEQ ID NO:1. As used herein, terms such as "North American PRRS virus peptide" mean a peptide that is expressed by a North American PRRS virus. Such a peptide can be, but is not necessarily, specific to North American PRRS viruses.

In a preferred embodiment, an isolated polynucleotide molecule of the present invention encoding a North American PRRS virus peptide comprises a sequence or sequences independently selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, and a sequence homologous to any of said sequences. Such isolated polynucleotide molecules are useful in plasmids or for preparing viral vectors for transfecting a suitable host cell to create a "helper" cell comprising one or more nucleotide sequences that encode a peptide encoded by a North American PRRS virus, wherein the genome sequence of said North American PRRS virus is the same as or homologous to an RNA sequence corresponding to SEQ ID NO:1, which helper cell is useful in the preparation of functional virions of genetically modified North American PRRS viruses of the present invention, which viruses have been genetically modified as described above so that they are missing from their RNA genome the sequence(s) encoding the peptide or peptides encoded by the helper cell.

Accordingly, the subject invention also includes plasmids and viral vectors comprising one or more nucleotide sequences encoding a peptide encoded by a North American PRRS virus, wherein the genome sequence of said North American PRRS virus is the same as or homologous to an RNA sequence corresponding to SEQ ID NO:1. Such plasmids of the invention can be based on those plasmids described above useful for preparing plasmids comprising a nucleotide sequence encoding a North American PRRS virus. Such viral vectors of the invention can be based on, for example, retrovirus vectors or adeno-associated viral vectors. These plasmids and viral vectors are useful for preparing the helper cells described in the preceding paragraph.

The present invention also thus provides a helper cell, i.e., a transfected host cell comprising one or more nucleotide sequences that encode a peptide encoded by a North American PRRS virus, wherein the genome sequence of said North American PRRS virus is the same as or homologous to an RNA sequence corresponding to SEQ ID NO:1. In preferred embodiments, the transfected host cell comprises a nucleotide sequence or sequences independently selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9 and a sequence homologous to any of said sequences. These helper cells are useful as described above for providing peptides for completing infectious RNA molecules deficient in sequences encoding the peptide(s) encoded by the helper cell so that functional virions of a genetically modified North American PRRS virus can be generated by the cell.

Suitable cells for this aspect of the invention include the cells described above which are suitable for expressing North American PRRS viruses, such as the porcine alveolar macrophage cells and the MARC-145 cells. However, practically any mammalian or avian cell can be used. As discussed above, if one wishes to obtain a transfected host cell capable of reinfection by PRRS virions, and thus able to generate multiple generations of functional genetically modified North American PRRS virions, porcine alveolar macrophage cells and MARC-145 cells are preferred.

The subject invention thus further provides a method for generating a functional virion of a genetically modified North American PRRS virus encoded by an RNA sequence corresponding to SEQ ID NO:1 or a sequence homologous thereto comprising one or more mutations that disable one or more peptide coding sequences, which method comprises transfecting a helper cell as described in the preceding paragraph with an infectious RNA molecule, plasmid, or viral vector encoding the genetically modified North American PRRS virus, which helper cell comprises a nucleotide sequence or sequences encoding the North American PRRS virus peptide or peptides of the disabled peptide coding sequence(s) of the genetically modified North American PRRS virus.

The subject invention further provides a method for generating a functional virion of a genetically modified North American PRRS virus encoded by an RNA sequence corresponding to SEQ ID NO:1 or a sequence homologous thereto comprising one or more mutations in one or more peptide coding sequences, which method comprises transfecting a suitable cell with both an infectious RNA molecule, plasmid, or viral vector encoding the genetically modified North American PRRS virus and a helper virus that expresses in the cell the North American PRRS virus peptide or peptides of the mutated peptide coding sequence or sequences of the modified North American PRRS virus, and separating genetically modified North American PRRS virions from the helper virus. Methods of separation are known in the art and include use of conditional lethal helper viruses that distinguish (kill) the helper virus under certain conditions wherein the expressed North American PRRS virus is not killed. Other known methods of separation include physical methods of separation subsequent to expression of both helper virions and North American PRRS virions, for example by density gradient centrifugation. Suitable cells for this method of the invention include the cells capable of infection by a PRRS virus, such as porcine alveolar macrophage cells and MARC-145 cells. Other cells which are able to be infected by a PRRS virus are described previously in this application, for example the MA-104 cell line or other cell lines derived from the MA-104 cell line. An example of a helper virus is a PRRS virus, preferably a North American PRRS virus isolate, such as P129. Any virus, either wild-type, isolated, or recombinant, that expresses PRRS peptides can be used as a helper virus.

Infectious RNA molecules, plasmids, and viral vectors that encode a genetically modified North American PRRS virus useful in either of the above methods for generating a functional virion of a genetically modified North American PRRS virus are those infectious RNA molecules, plasmids, and viral vectors described in this application.

H. Immunoprotective Genetically modified Nidovirales Viruses and Vaccines Comprising Them:

The subject invention further provides a genetically modified Nidovirales virus that is capable of eliciting an immunoprotective response in a mammal or a bird vaccinated therewith, which genetically modified Nidovirales virus is prepared by obtaining an isolated polynucleotide molecule comprising a DNA sequence encoding an infectious RNA molecule encoding a wild-type Nidovirales virus, genetically mutating the DNA sequence encoding the infectious RNA molecule encoding the wild-type Nidovirales virus so as to obtain an isolated polynucleotide molecule comprising a DNA sequence encoding an infectious RNA molecule encoding a genetically modified Nidovirales virus which virus is able to elicit an effective immunoprotective response against infection by the wild-type Nidovirales virus in a mammal or a bird, and expressing the genetically modified Nidovirales virus from the isolated polynucleotide molecule so obtained.

The subject invention further provides a method for preparing a genetically modified Nidovirales virus that is capable of eliciting an immunoprotective response in a mammal or a bird vaccinated therewith, which method comprises obtaining an isolated polynucleotide molecule comprising a DNA sequence encoding an infectious RNA molecule encoding a wild-type Nidovirales virus, genetically mutating the DNA sequence encoding the infectious RNA molecule encoding the wild-type Nidovirales virus so as to obtain an isolated polynucleotide molecule comprising a DNA sequence encoding an infectious RNA molecule encoding a genetically modified Nidovirales virus which virus is able to elicit an effective immunoprotective response against infection by the wild-type Nidovirales virus in a mammal or a bird, and expressing the genetically modified Nidovirales virus from the isolated polynucleotide molecule so obtained.

DNA sequences encoding infectious RNA molecule encoding a Nidovirales virus include the DNA sequences which are the same as or homologous to SEQ ID NO:1 described herein, which encode a North American PRRS virus. DNA sequences encoding infectious RNA molecules encoding Nidovirales viruses other than a North American PRRS virus are known in the art and can be obtained from known sources, for example the genetic databases cited above. Other examples of some DNA sequences encoding infectious RNA molecules encoding Nidovirales viruses which can be used in the subject invention include the DNA sequence encoding European PRRS virus described in Meulenberg, J. J. M., et al., 1993, supra; the DNA sequence encoding equine arteritis virus described in van Dinten, L. D., et al., 1997, Proc. Natl. Acad. Sci. USA, 94(3):991–6; and the DNA sequence encoding equine arteritis virus described in den Boon, J. A., et al., 1991, J. Virol. 65(6): 2910–20, all of which references are hereby incorporated in their entireties into the present application. Nidovirales viruses which can be genetically modified by means of the present invention can be any Nidovirales virus for which a coding DNA sequence is obtained. Some examples of Nidovirales viruses are described in previous sections of the present application.

Once a DNA sequence encoding an infectious RNA molecule encoding a Nidovirales virus is obtained, isolated polynucleotide molecules, for example plasmids, comprising the DNA sequence encoding an infectious RNA molecule encoding a Nidovirales virus can be synthesized using recombinant techniques described above.

The sequences encoding the infectious RNA molecule encoding a Nidovirales virus can be genetically mutated as described above for the North American PRRS virus so as to obtain Nidovirales viruses comprising genetic modifications such as an inability to cause disease in an animal infected therewith, inclusion of heterologous antigenic epitopes that are able to elicit an immunoprotective response in an animal, inclusion of heterologous antigenic epitopes that are detectable, and deletion of detectable antigenic epitopes. Such genetic modifications are described above. Genetic mutations so as to encode genetically modified Nidovirales viruses can occur in coding and/or noncoding regions of the DNA sequence encoding the infectious RNA molecule encoding the Nidovirales virus. In one embodiment, one or more genetic mutations occur in an ORF encoding a viral peptide of the Nidovirales virus.

"Wild-type Nidovirales virus", as used herein, means a Nidovirales virus whose genome has not intentionally been genetically mutated, such as a Nidovirales virus occurring in nature and isolates thereof.

The subject invention further provides a vaccine for protecting a mammal or a bird from infection by a Nidovirales virus, which comprises a genetically modified Nidovirales virus as described above in an amount effective to elicit an effective immunoprotective response against the wild-type Nidovirales virus in a mammal or a bird vaccinated therewith, and a carrier acceptable for pharmaceutical or veterinary use. These vaccines of the present invention can be formulated using the techniques for formulating vaccines described above.

The following examples are provided to merely illustrate aspects of the subject invention. They are not intended, and should not be construed, to limit the invention set forth in the claims and more fully described herein.

EXAMPLES

Example I

Preparation of an Infectious cDNA Clone of a North American PRRS Virus Isolate.

Source of PRRS virus and MARC-145 cells: A North American PRRS virus isolate designated P129 was obtained from Drs. Gregory W. Stevenson, William G. Van Alstine, and Charles L. Kanitz of Purdue University's Animal Disease Diagnostic Laboratory in West Lafayette, Ind. The P129 virus was originally isolated in the autumn of 1995 from a swine herd in southern Indiana experiencing a severe PRRS outbreak. This farm had no previous history of PRRS problems or PRRS vaccination. The P129 isolate was more virulent than several other field isolates from the same time period and geographic area, in that it produced more severe and more consistent respiratory disease in young pigs. The virus was initially isolated on primary porcine alveolar macrophage (the natural host cell), and subsequently passaged on MARC-145 cells (Kim, H. S. et al., 1993, Arch. Virol. 133:477–483). Genes encoding structural proteins of P129 were found to be homologous to corresponding known North American PRRS gene sequences.

The MARC-145 cell line that was used to propagate PRRS viruses is a clone of the MA-104 Rhesus Macaque Monkey Kidney cell line. The MARC-145 cells were obtained from the National Veterinary Services Laboratories (NVSL, Ames, Iowa) of the USDA. These cells have been tested and found negative for mycoplasmas and for common porcine extraneous agents. MARC-145 cells are routinely grown at 37 C in OptiMEM (Life Technologies Inc.) with 2% fetal bovine serum and antibiotics.

Five biological clones were plaque purified from the P129 virus stock, and these were designated P129A through P129E. Plaque purification was carried out by infecting monolayers of MARC-145 cells with P129 virus, adding an overlay of OptiMEM containing 1.25% SeaPlaque agarose (FMC BioProducts), 2% fetal bovine serum, and antibiotics. Plaques were clearly visible following incubation for 7 days, when 5 well-isolated plaques were picked and passaged onto fresh MARC-145 monolayers. When cytopathic effect (virus induced cell death) became apparent the progeny virus from each of these cultures was subjected to another round of plaque purification. One well-isolated plaque from each of the five clones was picked and expanded to produce large stocks. The 5 clones were tested for virulence in young pigs, either individually (clones A and E) or in combination (clones B–D, or clones A–E). In all cases, the plaque purified virus replicated well in pigs and caused clinical disease. The severity of clinical symptoms was less than that caused by the uncloned P129 virus, even when all five clones were used together. P129A was chosen for sequencing, and was used in subsequent molecular manipulations.

Determination of the genome sequence of P129A: Plaque purified virus P129A was used for sequence determination after 10 serial passages from the pig (including two plaque purifications and one subsequent passage). SEQ ID NO:1 shows the cDNA sequence corresponding to the P129A RNA genome. The genome is 15,395 nucleotides in length (excluding the polyadenosine tail), begins with ATGACGTA, and ends with CCGCMTT. A typical polyadenosine tail of 55 residues is also provided in SEQ ID NO:1.

For the structural genes of P129A (ORFs 2 through 7), which comprise the 3' 20% of the genome, various PCR primers were chosen based on several partial cDNA sequences of other North American PRRS virus isolates available in the public DNA sequence database GenBank (for example PRU00153). Purified viral RNA was reverse transcribed into cDNA using reverse transcriptase and random hexamer primers. This cDNA was then used in PCR with gene-specific primers. PCR products were excised from gels and T/A cloned into plasmid pCR2.1 (Invitrogen). For each primer pair, multiple plasmids (from independent PCR reactions) were DNA sequenced. Sequences were assembled using the Seqman program from the Lasergene package (DNASTAR, Inc). This permitted completing the sequence of positions 11,992 through 15,347 of the P129A genome.

Also in the GenBank database are a series of short sequences (approximately 218 nucleotides total) which comprise a portion of the ORF 1b gene of several isolates of PRRS virus. One of these (PPSSEQB) was used to design PCR primers (forward 5'-ACAGTTTGGTGATCTATG-3' (SEQ ID NO:10), corresponding to positions 9063–9080; reverse 5'-CAGATTCAGATGTTCAA-3' (SEQ ID NO:1 1), corresponding to positions 9252–9268). These amplified a 206 nucleotide fragments, which includes 171 nucleotides of new sequence from the P129A ORF1b gene, corresponds to positions 9081 to 9251. A new forward primer was designed within this region (5'-ACCTCGTGCTGTATGC-CGAATCTC-3' (SEQ ID NO:12), positions 9201–9224), and a matching primer was designed within ORF1b immediately upstream of ORF2 (5'-TCAGGCCTAAAGTTGGT-TCAATGA-3' (SEQ ID NO:13), positions 12,027–12,050). These primers were used in RT-PCR to amplify a 2850 nucleotide fragment of ORF1b, corresponding to positions 9201–12,050 of the P129A genome.

During RT-PCR amplification of ORF5 of another North American field isolate of PRRS virus, a minor band was seen which was smaller than the expected size. This was sequenced and found to have limited homology with ORF1a of Lelystad virus (resulting from false priming). New primers within this region were chosen to amplify P129A (forward 5'-GATGACTGGGCTACTGACGAGGAT-3' (SEQ ID NO:14), corresponding to positions 1587–1610; reverse 5'-AGAGCGGCTGGGATGACACTG-3' (SEQ ID NO:15), corresponding to positions 1877–1897). In addition to the product of 311 nucleotides (266 nucleotides of new P129A sequence between the primers corresponding to positions 1611–1876), a larger minor PCR product of 701 nucleotides was cloned and sequenced (656 nucleotides of new P129A sequence between the primers corresponding to positions 1611–2264). The larger band results from false priming of the reverse primer at positions 2265–2269.

The extreme 5' end of the genome of P129A was determined by 5' RACE (rapid amplification of cDNA ends) using a commercially available kit (Life Technologies Inc). Two nested reverse primers were chosen from within the known ORF1a sequence ("RACE2" 5'-CCGGGGAAGC-CAGACGATTGAA-3'(SEQ ID NO:16), positions 1917–1938; and "RACE3" 5'-AGGGGGAGCAAA-GAAGGGGTCATC-3' (SEQ ID NO:17), positions 1733–1756). RACE2 was used to prime cDNA synthesis, while RACE3 was used in PCR. The resulting PCR products were cloned and sequenced. The two longest products ended at precisely the same base (position 1 in SEQ ID NO:1).

The large gap between known sequence in ORF1a and ORF1b was bridged using long RT-PCR. Two new primers were used (forward 5'-AGCACGCTCTGGTGCAACTG-3' (SEQ ID NO:18), positions 1361–1380; reverse 5'-GC-CGCGGCGTAGTATTCAG-3' (SEQ ID NO:19), positions 9420–9438). The resulting 8078 nucleotide RT-PCR product was cloned and sequenced.

The extreme 3' end of the genome of P129A was determined by ligating the 3' and 5' ends of the viral RNA together and using RT-PCR to amplify the junction fragment. The resulting junction fragments were cloned and sequenced. Briefly, RNA extracted from pelleted virions was treated with tobacco acid pyrophosphatase (to remove 5' cap structures), then self-ligated with T4 RNA ligase (both from Epicentre Technologies). The primers used were 5'-CGCGT-CACAGCATCACCCTCAG-3' (SEQ ID NO:20) (forward, positions 15,218–15,239) and either 5'-CGGTAGGTTGGT-TAACACATGAGTT-3' (SEQ ID NO:21) (reverse, positions 656–680) or 5'-TGGCTCTTCGGGCCTATAAAATA-3' (SEQ ID NO:22) (reverse, positions 337–359). All of the resulting clones were truncated at the 5' end of the genome (the most complete came to within 57 nucleotides of the actual 5' end, as revealed by 5' RACE), however two of these clones contained the complete 3' end of the genome including the polyadenosine tail (42 and 55 adenosine residues in length). This completed the sequencing of the cDNA 15,450 base genome of PRRS isolate P129A, including polyA tail, as shown in SEQ ID NO:1.

Creation of an infectious full-length cDNA clone of P129A: A full-length infectious cDNA clone of P129A, designated pT7P129A, was assembled from four overlapping cloned RT-PCR products. The four RT-PCR products were first T/A cloned into plasmid pCR2.1 (Invitrogen) and transfected into Escherichia coli strain DH5-alpha. Bacterial colonies were screened, and those which contained inserts of the expected sizes in the "T7 to M13"0 orientation were chosen for sequencing and further manipulation. All four cloned RT-PCR products contained one or more non-silent mutations (deviations from the consensus nucleotide sequence for P129A of SEQ ID NO:1 which would result in a change in amino acid sequence of the encoded ORFs). These non-silent mutations (save one at position 12,622 in ORF 2) were repaired by subcloning fragments from other cloned RT-PCR products. The four repaired subgenomic clones were assembled into a full-length clone in a stepwise manner, using available restriction sites (see FIG. 1). The 5' and 3' ends of the cDNA corresponding to the P129A genome in pT7P129A were modified by the addition of a T7 promoter and appropriate restriction endonuclease sites. The construction of pT7P129A is described in further detail in the following paragraphs:

The 5' end of the genome (positions 1–1756), generated by 5'-RACE and cloned into pCR2.1 as described above, was modified to include a T7 promoter immediately upstream of the cDNA corresponding to the P129A genome and a PacI site for future cloning. A 3-way ligation was performed using the 1216 bp DsaI-BseRI fragment of this plasmid (containing bases 27–1242 of P129A), the 4407 bp BseRI-XbaI fragment of the same plasmid (containing bases 1243–1756 of P129A and the entire plasmid vector up to the XbaI site), and the following synthetic double-stranded adapter (SEQ ID NOS:23 and 24):

13,249 bp NdeI-SpeI fragment of pT7RG to yield plasmid "pT71A1B", which contains the first 12,050 bases of the P129A genome.

The fourth and final fragment of the P129A genome was derived by RT-PCR of ORFs 2 through 7, including the 3' non-translated region and a portion of the polyA tail. The forward primer was 5'-ACTCAGTCTAAGTGCTG-GAAAGTTATG-3' (SEQ ID NO:25) (positions 11,504–11,530) and the reverse primer was 5'-GGGATTTAAATATG-CATTTTTTTTTTTTTTTTTTTTTAATTGCGGCCGCAT-GGTTCTCG-3' (SEQ ID NO:26). The reverse primer contains the last 22 bases of the P129A genome (positions 15,374–15,395), a polyA tail of 21 bases, an NsiI site (ATGCAT) and a SwaI site (ATTTAAAT). Non-silent point mutations and a single base deletion were repaired by subcloning fragments from other clones. An additional non-silent point mutation at position 12,622 (A to G) was inadvertently introduced at this stage. This results in a change from glutamine to arginine near the C-terminus of the ORF2 protein (amino acid residue 189 of the 256 amino acids in ORF2, which does not affect the overlapping ORF 3). This mutation had no apparent influence on viral growth, in cell culture or in pigs, and was not repaired. This mutation served as a genetic marker to distinguish virus derived from the cDNA clone from possible contamination with parental P129A or other PRRS viruses. The plasmid was designated "p2_7D4". The structural genes of P129A were added to the rest of the genome by ligating the 3678 bp Eco47III-SpeI fragment of p2_7D4 to the 15,635 bp Eco47III-SpeI fragment of pT71A1B.

This yields the final construct "pT7P129A", which comprises cDNA corresponding almost identically to the entire genome of P129A (however, with only a 21 base polyA tail, as opposed to 55 base polyA tail) behind a T7 promoter, cloned into the pCR2.1 vector between unique restriction enzyme sites (PacI and SwaI). The total length of pTP7129A is 19,313 bp, and it is stable in E. coli strain DH5-alpha.

```
5'-CTAGATTAATTAATACGACTCACTATAGGGATGACGTATAGGTGTTGGCTCTATGC-3'

3'-TAATTAATTATGCTGAGTGATATCCCTACTGCATATCCACAACCGAGATACGGTGC-5'
   XbaI _____ T7 promoter      _____DsaI
        PacI                   P129A genome
```

The predicted transcript from the T7 promoter includes a single "G" residue from the promoter immediately upstream of the first "A" of the viral genome. A non-silent mutation at position 1230 (A to G) was repaired by replacing the 906 bp AatII-SacII fragment (bases 740–1645) with the same fragment from another clone. This plasmid was designated "pT7R3A-2".

The 8078 nucleotide PCR product described above was used to cover bases 1361–9438 of the P129A genome. A 58 bp deletion (positions 2535–2592) and 7 non-silent point mutations were corrected by subcloning fragments from other cloned RT-PCR products, yielding plasmid "pGAP10B-4". The 7837 bp Bsu36I-SpeI fragment from this plasmid was ligated to the 5482 bp Bsu36I-SpeI fragment from pT7R3A-2. The resulting plasmid "pT7RG" contains the first 9438 bases of the P129A genome behind the T7 promoter.

The 2850 nucleotide fragment of ORF1b described above (genome positions 9201–12,050) was corrected to repair non-silent mutations and designated "p1 B3A-2". The 2682 bp NdeI-SpeI fragment of this plasmid was ligated to the pT7P129A contains an A to G non-silent point mutation at position 12,622 that results in an arginine at position 189 of ORF2 rather than a glutamine (as is encoded by SEQ ID NO:1) and a silent C to T mutation at position1559. Neither of these mutations affected viral growth under the conditions examined, both in cell culture and in pigs. For example, pT7P129A was used for in vitro transcription and the resulting RNA transcripts produced live North American PRRS virus when transfected into MARC-145 cells, thus demonstrating that this full-length clone is infectious.

In vitro transcription and transfection of RNA transcripts: In plasmid pT7P129A there are two T7 promoters in tandem upstream of the viral genome. One of these is positioned immediately upstream of the viral genome and was built into the PCR primer as described above. The other is present in the pCR2.1 cloning vector and is located outside of the multiple cloning site (initiating transcription 44 bases upstream of the viral genome). PacdI was used to cut between these T7 promoters prior to in vitro transcription to generate a transcript that is closer to authentic viral RNA (a single extra G immediately upstream the viral genome, as opposed to 44 extra bases from the distal T7 promoter). In addition, pT7P129A was cut with SwaI prior to in vitro transcription. The resulting run-off transcripts include a 21 base long polyA tail and nine non-PRRS nucleotides, including an NsiI site (which was not used to linearize the plasmid, since the site also occurs once in the viral genome). The digested plasmid was purified by phenol extraction and ethanol precipitation prior to use.

A commercial kit (T7 Cap-Scribe, Boehringer Mannheim) was used for in vitro transcription. The DNA pellet from above, containing about 0.6 μg of PacI/SwaI digested pT7P129A, was resuspended in 20 μl of T7 Cap-Scribe buffer/T7 polymerase and incubated at 37° C. for 30 minutes. A portion of the reaction was analyzed by agarose gel electrophoresis and shown to contain full-length RNA transcripts in addition to the expected DNA bands of 15,445 bp and 3868 bp. The in vitro transcription reaction was used fresh, immediately following incubation, without purification. Freshly confluent monolayers of MARC-145 cells were washed once in OptiMEM (without serum), and covered with 1 ml per 35 mm well of OptiMEM (without serum) containing 500 μg/ml DEAE dextran (molecular weight approx. 500,000, Pharmacia Biotech). In vitro transcription reaction (15 μl) was added immediately. After 1 hour at 37° C., the transfection mixture was removed, monolayers were washed once with PBS and overlaid with 1.25% SeaPlaque agarose (FMC corporation) in OptiMEM with 2% fetal bovine serum and antibiotics. After 5 days at 37° C., a single plaque was visible. This virus was designated "rP129A-1" and was expanded on MARC-145 cells and characterized in cell culture and in pigs. Subsequent transfections of in vitro transcribed RNA from pT7P129A, using both DEAE dextran and electroporation, have yielded many additional plaques.

Characterization of recombinant virus rP129A-1: There are no apparent differences in growth kinetics, yield, or plaque morphology between cDNA-derived recombinant virus rP129A-1 and its non-recombinant parent P129A. As discussed above, there are two differences in nucleotide sequence between the coding sequence of pT7P129A and the consensus sequence of P129A (shown in SEQ ID NO:1). Firstly, at position 1559 pT7P129A contains a T, whereas P129A contains a C (this is a silent mutation). Secondly, at position 12,622 pT7P129A contains a G, whereas P129A contains an A (this is the glutamine to arginine change in ORF2 described above). In order to rule out the possibility that rP129A-1 is actually a non-recombinant PRRS virus contaminant, RT-PCR and sequencing were performed on the regions surrounding these two differences. In the case of both genetic markers, rP129A-1 was identical to plasmid pT7P129A and different from parental virus P129A, thus confirming that rP129A-1 is derived from the infectious cDNA clone.

Figure 2:
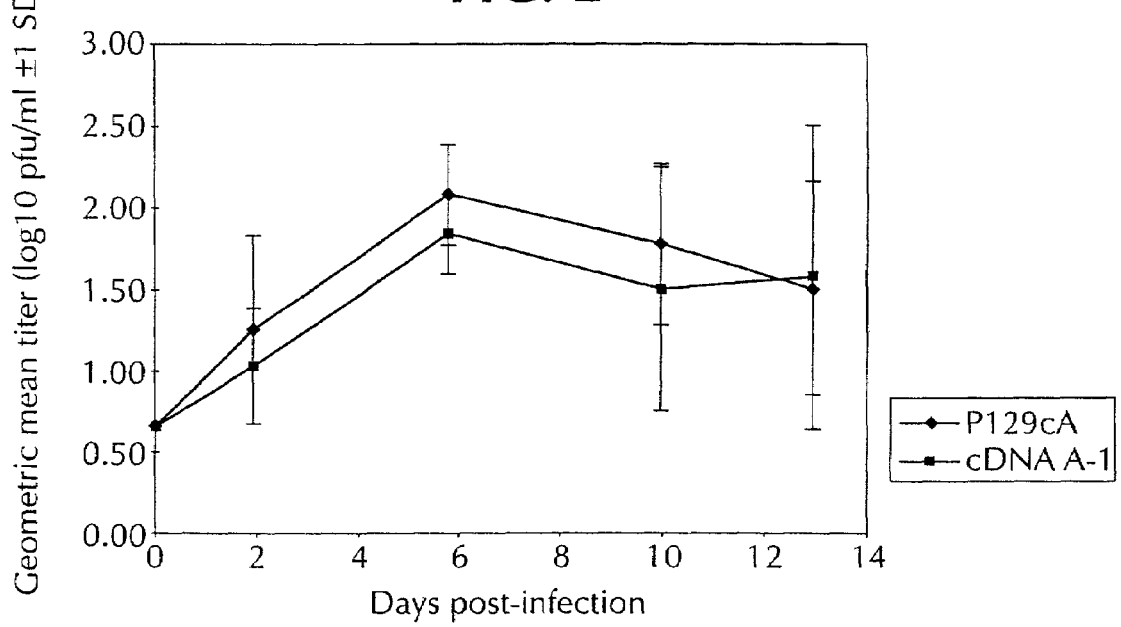
FIG. 2: Serum viremia following infection with P129A or recombinant PRRS virus rP129A-1. Determined by plaque assay on MARC-145 cells. The lower limit of detection is 5 pfu/ml (or 0.7 on the log scale).
Figure 3:
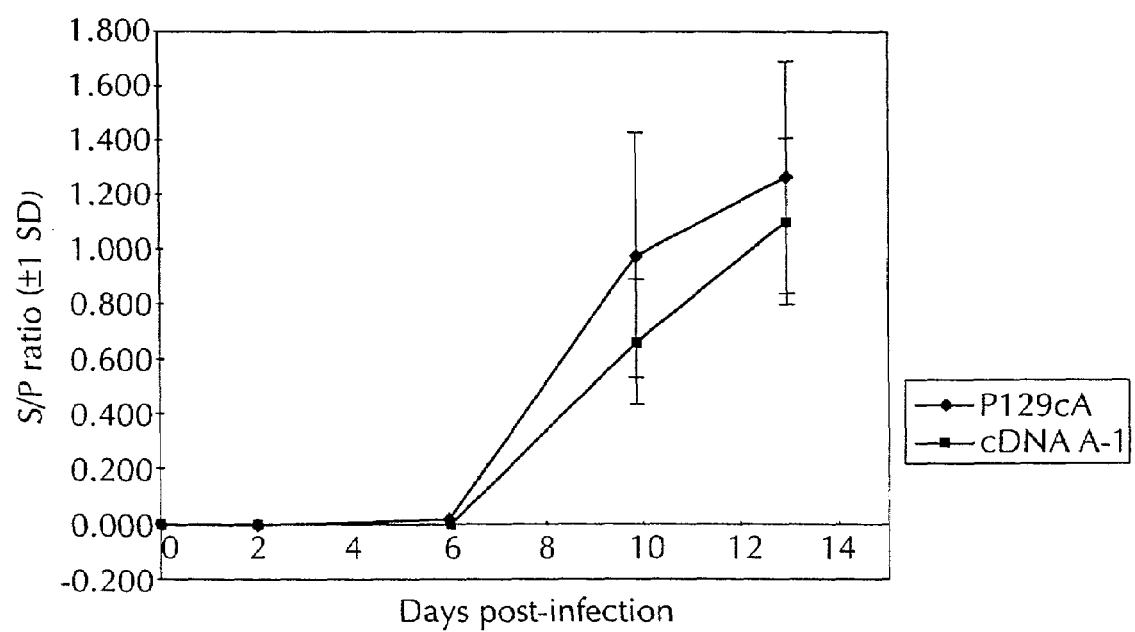
FIG. 3: Anti-PRRS virus serum antibody following infection with P129A or recombinant PRRS virus rP129A-1. Determined by HerdChek PRRS ELISA assay (IDEXX (Westbrook, Me., USA)).

Characterization of recombinant virus rP129A-1 in pigs: The cDNA-derived virus rP129A-1 was compared to its non-recombinant parent P129A for its ability to infect and cause clinical disease in young pigs. Three groups of 10 pigs each from a PRRS-negative herd were infected at 4 weeks of age with either P129A, rP129A-1, or mock-infected with cell culture medium. Clinical signs, rectal temperatures, and body weights were monitored. Blood was collected on days 0, 2, 6, 10, and 13 post-infection for determination of serum viremia (by plaque assay on MARC-145 cells, FIG. 2) and serum antibody (by ELISA using HerdChek PRRS from IDEXX, FIG. 3). Gross and microscopic lesions of the lung were observed upon necropsy. There were no significant differences between the two virus-infected groups, indicating that rP129A-1 replicates in pigs and causes clinical disease which is quantitatively and qualitatively similar to its non-recombinant parent virus.

Example II

Deletion of ORF7 (Nucleocapsid Gene) from the North American PRRS Virus; Preparation of a Negatively-Marked, Replication-Defective Vaccine Thereby.

The viral nucleocapsid gene (ORF7) was partially deleted from an infectious cDNA clone of the PRRS virus of the present invention. The resulting recombinant modified PRRS virus would be expected to be replication-defective in pigs. This recombinant modified PRRS virus could be used as a vaccine to induce an immune response to the other PRRS virus proteins without the risks of clinical disease, spread to non-vaccinated animals, or reversion to virulence associated with attenuated live vaccines. In addition to being very safe, such a vaccine virus would also be "negatively marked", in the sense that it would allow exposure to field isolates of PRRS virus to be determined serologically, even in the presence of antibody to the vaccine virus. Antibodies to the ORF7 protein are commonly found in the sera of PRRS virus-infected pigs, whereas pigs vaccinated with an ORF7-deleted PRRSV would lack antibodies to the ORF7 protein.

Deletion of ORF7 from an infectious clone was accomplished as follows: Plasmid p2_7D-4 (see FIG. 1) was used as template in PCR to amplify the 5' and 3' flanking regions upstream and downstream of ORF7. The upstream flank forward primer 5'-ATTAGATCTTGCCACCATGGTGGG-GAAATGCTTGAC-3' (SEQ ID NO:27) (which binds to genome positions 13,776–13,791 near the beginning of ORF5 and contains additional restriction sites which are irrelevant to the current cloning) and the upstream flank reverse primer 5'-CTTTACGCGTTTGCTTAAGT-TATTTGGCGTATTTGACAAGGTTTAC-3' (SEQ ID NO:28) (which binds to genome positions 14,857–14,902 at the junction of ORFs 6 and 7) amplified a fragment of 1147 bp. The reverse primer introduced MluI and AflII sites and a single base change at position 14,874, destroying the ATG start codon for ORF7 without altering the tyrosine encoded in the overlapping ORF6. For the downstream flank, the forward primer 5'-CAACACGCGTCAGCAAAA-GAAAAAGAAGGGG-3' (SEQ ID NO:29) (positions 14,884–14,914 near the 5' end of ORF7, introduced an MluI site) and reverse primer 5'-GCGCGTTGGCCGAT-TCATTA-3' (SEQ ID NO:30) (downstream of the viral genome in the pCR2.1 plasmid) amplified a 462 bp fragment. A 3-way ligation was performed, using the 611 bp BstEII-MluI fragment of the upstream flank PCR product, the 575 bp MluI-SpeI fragment of the downstream flank PCR product, and the 6653 bp BstEII-SpeI fragment from plasmid p2_7D-4 (all fragments were gel purified following digestion). The resulting plasmid p2_7Ddelta7+7023 was deleted in the first seven amino acids of ORF7, and lacks a functional ATG start codon. Two new restriction sites which are absent in both the viral genome and the plasmid backbone, AflII and MluI, have been inserted to facilitate directional cloning of foreign genes into the space previously occupied by the 5' end of ORF7.

The changes made in p2_7Ddelta7+7023 were incorporated into a full-length genomic clone by ligating the 3683 bp Eco47III-SpeI fragment of p2_7Ddelta7+7023 with the 15,214 bp Eco47III-SpeI fragment of pCMV-S-p129. The resulting plasmid pCMV-S-p129delta7+7023 was used to transfect cells.

Since nucleocapsid is essential for viral growth, it is necessary to provide this protein in order to allow generation and replication of an ORF7-deficient PRRS virus. This can be accomplished using a helper virus or a complementing cell line, for example. ORF7-expressing MARC-145 cell lines could be created by stably transfecting cells with a plasmid containing both the ORF7 gene from P129A and the neomycin resistance gene. After selecting for neomycin resistance using the antibiotic G418, single-cell colonies could then be expanded and characterized. Clonal MARC-145-derived cell lines that are positive for ORF7 expression by both immunofluorescence and RT-PCR could be transfected with RNA from pT7P129delta7 in order to generate ORF7-deficient P129 virus.

Similar strategies can be used to generate PRRS viruses deficient in other structural genes (ORFs 2, 3, 4, 5, or 6), or deficient in all or portions of non-structural genes 1a and 1b. In addition, multiple deletions can be engineered into a single PRRS virus, and these can be grown in complementing cells which provide all necessary functions. Such gene-deficient PRRS viruses are likely to be either partially or completely attenuated in pigs, making them useful as vaccines against PRRS. They can also be used to distinguish vaccinated animals from animals infected with a wild-type PRRS virus as discussed above and/or as vectors for vaccinating animals with epitopes of other porcine pathogens (see Example III, below).

Example III

Insertion of Heterologous Genes into the North American PRRS Virus Genome; use of PRRS Virus as a Vector, and a Positively-Marked North American PRRS Virus.

In Example II, above, AflII and MluI restriction enzyme sites were inserted into the region formerly occupied by the 5' end of ORF7. These sites are absent in the P129A genome and in the pCR2.1 and pCMV plasmids, and can be used in the directional cloning of foreign (heterologous) genes into the viral genome for expression. Potential leader-junction sites for transcription of the ORF7 subgenomic RNA at positions 14,744–14,749 (ATMCC) and 14,858–14,863 (TAAACC) are not affected by deletion of the ORF7 coding sequence, and can function in transcription of a foreign gene. Foreign (heterologous) genes can include genes from other PRRS virus isolates or genotypes, and/or genes from other non-PRRS pathogens, either pathogens that infect swine or pathogens that infect mammals other than swine, or avians.

In addition, these foreign genes (or portions thereof) can provide antigenic epitopes which are not normally found in swine. Such epitopes can be used to "positively mark" a vaccine, so that successful vaccination can be monitored serologically, even in the presence of antibody to field or conventional vaccine strains of PRRS virus. A positive marker needs not be a separate expression cassette. An antigenic epitope can be fused to a structural gene of the PRRS virus. For example, the upstream flank reverse primer described in Example I, above, can be extended in such a way as to add a carboxyl-terminal fusion of a non-PRRS virus antigenic epitope to the ORF6 membrane protein. The presence of antibody to this epitope in swine indicates successful vaccination.

Example IV

Cellular Expression of a PRRS Virus by Direct Transfection of cDNA into Cells.

The eukaryotic expression vector pCMV-MC1 (SEQ ID NO:31) was derived from the commercially available plasmid pCMVbeta (Clontech) by replacing the LacZ coding sequence between two Not I sites with a linker containing Not I, EcoR V, Avr II, Bgl II, C/a I, Kpn I, Pac I, Nhe I, Swa I, Sma I, Spe I and Not I sites. Modification of the human CMV immediate early promoter was accomplished by substituting the sequence between the Sac I and the second Not I sites of pCMV-MC1 with a synthetic linker (shown below). The linker contains a half site for Sac I following by Pac I, Spe I and a half site for Not I. After annealing the two single stranded oligonucleotides, the linker was cloned into pCMV-MC1 between the Sac I and Not I sites, and a selected clone was designated pCMV-S1. The Spe I site of pCMV-S1 could not be cut, possibly due to a mistake in the oligo sequence. Therefore, the fragment between Pac I and Hind III in pCMV-S1 was replaced with Pac I (at position 877)-Hind III (at position 1162) fragment from pCMV-MC1. Thus, a Spe I site was regained. This final construct (pCMV-S) was used to clone the full length P129 genome.

Linker sequence (SEQ ID NOS:32 and 33):

```
    5' CGTTAATTAAACCGACTAGTGC   3'

3' TCGAGCAATTAATTTGGCTGATCACGCCGG 5'
         PacI         SpeI
    SacI                        NotI
```

The sequence immediately upstream of the 5' end of the P129 genome was modified to contain proper spacing and a convenient restriction enzyme site (Pac I). This was done by designing appropriate PCR primers (SEQ ID NOS:34 and 35) for amplification from pT7P129. After digestion with Pac I and Aat II, this PCR fragment was subcloned into the Pac I and Aat II sites of pT7RG (FIG. 1). The resulting plasmid was designated pT7RG-deltaT7.

The final construction was completed by subcloning the viral sequences from pT7RG-deltaT7 at the Pac I and Nde I sites into pT7P129, creating pT7P129-deltaT7. The full length P129 genome was digested from pT7P129-deltaT7 at Pac I and Spe I and transferred into pCMV-S at the Pac I and Spe I sites. This constructed was named pCMV-S-P129.

The sequence of the region of modification between the CMV promoter TATA box and the 5' end of the P129 sequence in pCMV-S-P129 is shown in SEQ ID NO:36 and schematically presented below:

```
    TATATAAGCAGAGCTCGTTAATTAAACCGTCATGACGTATAGGTGTTGGC
 5'    TATA box   Sac I   Pac I      Start of P129       3'
```

To test the use of the CMV promoter to initiate PRRS virus infection in cells, pCMV-S-P129 plasmid DNA (0.5 or 1.0 μg) was transfected into MARC-145 cells by lipofection using Lipofectamine™ (Life Technologies Inc.). PRRS virus specific cytopathic effect was observed after transfection and the presence of PRRS virus antigen was determined by the immunofluorescent antibody test.

PRRS virus was generated efficiently from pCMV-S-P129, and the progeny virus could be passaged on MARC-145 cells. This demonstrates that a PRRS virus infection can be initiated directly from a plasmid cDNA encoding a PRRS virus, without an in vitro transcription step. Furthermore, pCMV-S-P129 generated a greater amount of progeny virus compared to plasmids wherein the 3' end of the pCMV promoter was not immediately in front of the start of the sequence encoding the North American PRRS virus.

Example V

Deletion of ORF4 from the North American PRRS Virus; Preparation of a Replication-Defective Vaccine Thereby.

A portion of the gene for ORF4, which encodes a membrane glycoprotein, was deleted from an infectious cDNA clone of the PRRS virus of the present invention. The resulting recombinant modified PRRS virus is expected to be replication-defective in pigs and to induce an immune response to the other PRRS virus proteins without the risks of clinical disease, spread to non-vaccinated animals, or reversion to virulence associated with attenuated live vaccines.

Deletion of ORF4 from an infectious clone was accomplished as follows. Plasmid p2_7D-4 (see FIG. 1) was used as template in PCR to amplify the 5' and 3' flanking regions upstream and downstream of ORF4. The upstream flank forward primer was 5'-AGGTCGACGGCGGCAATTG-GTTTCACCTAGAGTGGCTGCGTCCCTTCT-3' (SEQ ID NO:37). This primer binds to genome positions 13194–13241, near the beginning of ORF4, and introduces a mutation at position 13225 which destroys the ATG start codon of ORF4 without altering the overlapping amino acid sequence of ORF3. The upstream flank reverse primer was 5'-TCTTAAGCATTGGCTGTGATGGTGATATAC-3' (SEQ ID NO:38). This primer binds to genome positions 13455–13477 within the ORF4 coding region, downstream of ORF3, and introduces an AflII site. For the downstream flanking region, the forward primer was 5'-CTTCT-TAAGTCCACGCGTTCTTCTTGCCTTTTC-TATGCTTCT-3' (SEQ ID NO:39). This primer binds to genome positions 13520–13545 in the middle of ORF4, and introduces Af/II and MluI sites for directional cloning of foreign genes. The reverse primer was 5'-TGCCCGGTC-CCTTGCCTCT3' (SEQ ID NO:40). This primer binds to genome positions 14981–14999 in the ORF7 coding sequence. A three-way ligation was performed using the SalI-AflII fragment of the upstream flank PCR product, the AflII-BstEII fragment of the downstream flank PCR product, and the SalII-BstEII fragment from plasmid p2_7D-4. All fragments were gel-purified following digestion. The resulting plasmid p2_7D-4delta4N has 42 bases of the central portion of ORF4 deleted and replaced with a 15 base artificial cloning site. The cloning site contains two restriction sites (AflII and MluI) that are absent from both the viral genome and the plasmid backbone. These can be used to facilitate directional cloning of foreign genes into the space previously occupied by ORF4. The cloning site also contains a stop codon (TAA) that is in frame with ORF4 and further assures that functional ORF4 protein is not produced.

It was found that a more extensive deletion of the ORF4 coding sequence could be made without interfering with expression of the downstream ORF5 envelope gene. In this case a shorter downstream flanking region was amplified by PCR using the same template and reverse primer, and using forward primer 5'-GTTTACGCGTCGCTCCTTGGTG-GTCG-3' (SEQ ID NO:41). This primer binds to genome positions 13654–13669 near the 3' end of ORF4, and contains an AflI site. Two-way ligation between the AflII-BstEII fragment of the downstream flank PCR product and the AflII-BstEII fragment from plasmid p2_7D-4delta4N yielded the new plasmid p2_7D-4delta4NS. This plasmid has 176 bases of the ORF4 coding sequence deleted and replaced with the 15 base cloning site.

The changes made in p2_7D-4delta4N and p2_7Ddelta4NS were incorporated into the full-length genomic clone by replacing the BsrGI-SpeI fragment from pCMV-S-P129 with the modified BsrGI-SpeI fragments from p2_7D-4delta4N and p2_7D4delta4NS. The resulting plasmids pCMV-S-P129delta4N and pCMV-S-P129delta4NS were used to transfect cells.

In contrast to pCMV-S-P129, transfection of MARC-145 cells with plasmids pCMV-S-P129delta4N or pCMV-S-P129delta4NS did not result in viral plaques or fluorescent foci. Individual transfected cells could be seen to be producing the ORF7 nucleocapsid protein, suggesting that the ORF4 gene product is not required for RNA replication or expression of viral genes, but is essential for release of infectious progeny virus. Since deletion of ORF4 is lethal to virus replication, it is necessary to provide this protein. This can be accomplished by using a complementing cell line. We created ORF4-expressing MARC-145 cell lines by stable transfecting cells with a plasmid containing both ORF4 and the neomycin resistance gene. After selection for neomycin resistance using the antibiotic G418, single-cell colonies were expanded and characterized. After transfection with pCMV-S-P129delta4NS, three ORF4-expressing cell clones yielded live virus that could be propagated in these cells but not in MARC-145 cells. One of these, MARC400E9, was further characterized. Immunofluorescent staining for viral nucleocapsid in MARC400E9 cells transfected with plasmid pCMV-S-P129delta4NS was positive.

Example VI

Use of Gene-Deleted PRRS Virus as a Vector for Expression of Foreign Genes.

In order to determine whether heterologous genes can be expressed from a gene-deleted PRRS virus, we inserted a copy of green fluorescent protein (GFP) into the site of ORF4 deletion in plasmid pCMV-S-P129delta4N. The GFP gene was amplified from a commercially available plasmid vector using PCR primers that introduced an AflI site at the 5' end of the gene and an MluI site at the 3' end of the gene. The resulting plasmid pCMV-S-P129delta4N-GFP was used to transfect MARC-145 and MARC400E9 cells. As anticipated, MARC-145 cells did not support replication of the ORF4-deleted virus. Single green cells resulting from primary tranfection were seen under the UV scope, indication that GFP was being expressed, but the virus did not spread to neighboring cells and no CPE was observed. In contrast, large green foci were observed in transfected MARC400E9 cells. Visible plaques formed and merged, destroying the monolayer. These results indicate that foreign genes can be expressed from ORF4-deleted PRRS virus, and that increasing the size of the viral genome by 692 bases (4.5%) does not interfere with packaging of the viral RNA into infectious particles.

Example VII

Use of Replication-Competent PRRS Virus as a Vector for Expression of Foreign Genes.

In order to determine whether heterologous genes can be expressed from a replication-competent PRRS virus, we inserted a copy of GFP into the region between ORF1b and ORF2. Since the leader/junction (L/J) sequence for ORF2 lies within ORF1b, this L/J sequence was used to drive expression of the GFP gene and a copy of the ORF6 L/J sequence was inserted downstream from GFP to drive expression of ORF2.

Plasmid p2_7D-4 (see FIG. 1) was used as template in PCR to amplify the 5' and 3' flanking regions upstream and downstream of the insertion site. The upstream flank forward primer was 5'-AACAGAAGAGTTGTCGGGTC-CAC-3' (SEQ ID NO:42). This primer binds to genome positions 11699–11721 in ORF1b. The upstream flank reverse primer was 5'-GCTTTGACGCGTCCCCACT-TAAGTTCAATTCAGGCCTAAAGTTGGTTCA-3' (SEQ ID NO:43). This primer binds to genome positions 12031–12055 in ORF1b and adds AflII and MluI sites for directional cloning of foreign genes between ORF1b and ORF2. The downstream flank forward primer was 5'-GC-GACGCGTGTTCCGTGGCAACCCCTT-TAACCAGAGTTTCAGCGGAACAATGAAATGGG GTCTATACAAAGCCTCTTCGACA-3' (SEQ ID NO:44). This primer binds to genome positions 12056–12089 in ORF2 and contains an MluI site followed by the 40 bases that precede the start of ORF6 (containing the ORF6 L/J sequence). The downstream flank reverse primer was 5'-AA-CAGAACGGCACGATACACCACAAA-3' (SEQ ID NO:45). This primer binds to genome positions 13819–13844 in ORF5. A three-way ligation was performed using the Eco47III-MluI fragment of the upstream flank PCR product, the MluI-BsrGI fragment from the downstream flank PCR product, and the Eco47III-BsrGI fragment from pCMV-S-P129. The resulting plasmid pCMV-S-P129-1bMCS2 contains the entire P129 genome with a cloning site and an additional L/J site between ORF1b and ORF2. The plasmid produces functionally normal virus when transfected into MARC-145 cells.

The GFP gene from a commercially available plasmid was PCR amplified using primers that add an AflII site to the 5' end and an MluI site to the 3' end of the gene. After digestion of the PCR fragment and PCMV-SP129-1bMCS2 with Af/II and MluI, the insert was ligated into the vector to yield plasmid pCMV-S-P129-1bGFP2. This plasmid produced green plaques when transfected into MARC-145 cells. The resulting virus could be passaged onto MARC-145 cells and continued to produce green plaques when observed under the UV scope. Thus, foreign genes may be expressed from replication-competent PRRS virus vectors. The P129-1bGFP2 virus contains a genome which is 774 bases (5%) longer than that of its P129 parent, yet it is packaged normally.

DEPOSIT OF BIOLOGICAL MATERIALS

The following biological material was deposited with the American Type Culture Collection (ATCC) at 10801 University Blvd., Manassas, Va., 20110-2209, USA, on Nov. 19, 1998 and were assigned the following accession numbers:

| Plasmid | Accession No. |
|---|---|
| plasmid pT7P129A | 203488 |
| plasmid pCMV-S-P129 | 203489 |

All patents, patent applications, and publications cited above are incorporated herein by reference in their entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A recombinant North American PRRS virus population encoded by an isolated polynucleotide molecule comprising a DNA sequence encoding an infectious RNA molecule encoding a North American PRRS virus, wherein said DNA sequence is SEQ ID NO: 1.

2. A recombinant North American PRRS virus population encoded by an isolated polynucleotide molecule comprising a DNA sequence encoding an infectious RNA molecule encoding a North American PRRS virus, wherein said DNA sequence is SEQ ID NO:.1 or a sequence that hybridizes to the, complement of SEQ ID NO:1 under highly stringent conditions, wherein said highly stringent conditions comprise hybridization to filter-bound DNA in 0.5 M $NaHPO_4$, 7% SDS, 1mM EDTA at 65° C., and washing in 0.1×SSC/ 0.1% SDS at 68° C.

* * * * *

SEQUENCE LISTING

<160> NUMBER OF SEQ ID NOS: 45

<210> SEQ ID NO 1
<211> LENGTH: 15450
<212> TYPE: DNA
<213> ORGANISM: Artificial Sequence
<220> FEATURE:
<223> OTHER INFORMATION: Description of Artificial Sequence: cDNA
      corresponding to North American Porcine Reproductive And
      Respiratory Syndrome (PRRS) Virus Genome.

<400> SEQUENCE: 1

```
atgacgtata ggtgttggct ctatgccacg gcatttgtat tgtcaggagc tgtgaccatt      60
ggcacagccc aaaacttgct gcacggaaaa cgcccttctg tgacagcctt cttcagggga     120
gcttaggggt ctgtccctag caccttgctt ctggagttgc actgctttac ggtctctcca     180
cccctttaac catgtctggg atacttgatc ggtgcacgtg cacccccaat gccagggtgt     240
```

-continued

```
ttatggcgga gggccaagtc tactgcacac gatgtctcag tgcacggtct ctccttcctc      300
tgaatctcca agttcctgag cttggggtgc tgggcctatt ttataggccc gaagagccac      360
tccggtggac gttgccacgt gcattcccca ctgtcgagtg ctcccccgcc ggggcctgct      420
ggctttctgc gatctttcca attgcacgaa tgaccagtga aaacctgaac tttcaacaaa      480
gaatggtgcg ggttgcagct gagatttaca gagccggcca actcacccct gcagttttga      540
aggctctaca agtttatgaa cggggttgtc gctggtaccc cattgtcgga cctgtccctg      600
gagtggccgt tcacgccaac tccctacatg tgagtgacaa acctttcccg ggagcaactc      660
atgtgttaac caacctaccg ctcccgcaga ggcccaagcc tgaagacttt tgccctttg      720
agtgtgctat ggctgacgtc tatgacatta gccatgacgc cgtcatgtat gtggccagag      780
ggaaagtctc ctgggcccct cgtggcgggg atgaagtgaa atttgaaacc gtccccgaag      840
agttgaagtt gattgcgaac cgactccaca tctccttccc gccccaccac gcagtggaca      900
tgtctgagtt tgccttcata gccctggga gtggtgtctc cttgcgggtc gagcaccaac      960
acggttgcct tccgctgat actgtccctg aagggaactg ctggtggtgc ttgtttgact     1020
tgctcccacc ggaagttcag aataaagaaa ttcgccgtgc taaccaattt ggctatcaaa     1080
ccaagcatgg tgtccctggc aagtacctac agcggaggct gcaagttaat ggtctccgag     1140
cagtgactga tacagatgga cctattgtcg tacagtactt ctctgttagg gagagttgga     1200
tccgccactt cagactggcg gaagaaccta gcctccctgg gtttgaagac ctcctcagaa     1260
taagggtaga gcctaatacg tcgccattgg gtggcaaggg tgaaaaaatc ttccggtttg     1320
gcagtcacaa gtggtacggt gctggaaaga gagcaaggag agcacgctct ggtgcaactg     1380
ccacggtcgc tcactgcgct ttgcccgctc gcgaagccca gcaggccaag aagctcgagg     1440
ttgccagcgc caacagggct gagcatctca gtactattc cccgcctgcc gacgggaact     1500
gtggttggca ctgcatttcc gccattacca accggatggt gaattccaaa tttgaaacca     1560
ctcttcccga gagagtgaga ccttcagatg actgggctac tgacgaggat cttgtgaata     1620
ccatccaaat cctcaggctc cccgcggcct tggacaggaa cggtgcttgt gctggcgcca     1680
agtacgtgct caagctggaa ggtgagcact ggaccgtctc tgtgacccct gggatgaccc     1740
cttctttgct cccccttgaa tgtgttcagg gttgttgtga gcataagagc ggtcttggtt     1800
tcccagacgt ggtcgaagtt tccggatttg accctgcctg tcttgaccga cttgctgaga     1860
taatgcactt acctagcagt gtcatcccag ctgctctggc cgagatgtcc gacgacttca     1920
atcgtctggc ttccccggcc gccactgtgt ggactgtttc gcaattcttt gcccgccaca     1980
gaggaggaga gcatcctgac caggtgtgct tagggaaaat tatcaaccct tgtcaggtga     2040
ttgaggaatg ctgctgttcc cggaacaaag ccaaccgggc taccccggaa gaggttgcgg     2100
caaaagttga ccagtacctc cgtggtgcag caagccttgg agaatgcttg gccaagcttg     2160
agagggctcg cccgccgagc gcgatggaca cctcctttga ttggaatgtt gtgcttcctg     2220
gggttgagac ggcggatcag acaaccaaac agctccatgt caaccagtgc gcgcgctctg     2280
ttcctgtcgt gactcaagag ccttttggaca gagactcggt ccctctgacc gccttctcgc     2340
tgtccaattg ctactaccct gcacaaggtg acgaggtccg tcaccgtgag aggctaaact     2400
ccgtgctctc taagttggag ggggttgttc gtgaggaata tgggctcacg ccaactggac     2460
ctggcccgcg acccgcactg ccgaacgggc tcgacgagct taaagaccag atggaggagg     2520
atctgctgaa attagtcaac gcccaggcaa cttcagaaat gatggcctgg gcagccgagc     2580
aggttgatct aaaagcttgg gtcaaaaatt acccacggtg gacaccgcca cccctccac     2640
```

-continued

```
caagagttca gcctcgaaaa acgaagtctg tcaagagctt gctagagaac aagcctgtcc    2700
ctgctccgcg caggaaggtc agatctgatt atggcagccc gattttgatg ggcgacaatg    2760
ttcctaacgg ttgggaagat tcgactgttg gtggtcccct tgacctttcg gcaccatccg    2820
agccgatgac acctctgagt gagcctgtac ttatttccag gccagtgaca tctttgagtg    2880
tgccggcccc agttcctgca ccgcgtagag ctgtgtctcg accgatgacg ccctcgagtg    2940
agccaatttt tgtgtctgca ctgcgacaca aatttcagca ggtggaaaaa gcaaatctgg    3000
cggcagcagc gccgatgtac caggacgaac ccttagattt gtctgcatcc tcacagactg    3060
aatatggggc ttctccccta acaccaccgc agaacgtggg cattctggag gtaaggggc     3120 aagaagctga ggaagttctg agtgaaatct cggatattct gaatgatacc aaccctgcac    3180
ctgtgtcatc aagcagctcc ctgtcaagtg ttaggatcac acgcccaaaa tactcagctc    3240
aagccattat cgacttgggc gggccctgca gtgggcacct ccaaagggaa aagaagcat     3300 gcctccgcat catgcgtgag gcttgtgatg cggccaagct tagtgaccct gccacgcagg    3360
aatggctttc tcgcatgtgg atagggtgg acatgctgac ttggcgcaac acgtctgctt     3420
accaggcgtt tcgcaccta gatggcaggt ttgggttcct cccaaagatg atactcgaga     3480
cgccgccgcc ctaccgtgt gggttttgta tgttgcctca caccctgca ccttccgtga      3540 gtgcagagag cgaccttacc atcggttcag tcgccactga agatattcca cgcatcctcg    3600
ggaaaataga aaataccggt gagatgatca accaggacc cttggcatcc tctgaggaag     3660
aaccggtata caaccaacct gccaaagact cccggatatc gtcgcggggg tctgacgaga    3720
gcacagcagc tccgtccgca ggtacaggtg gcgccggctt atttactgat ttgccacctt    3780
cagacggcgt agatgcggac ggtgggggc cgttgcagac ggtaagaaag aaagctgaaa     3840
ggctcttcga ccaattgagc cgtcaggttt taacctcgt ctcccatctc cctgtttttct    3900 tctcacacct cttcaaatct gacagtggtt attctccggg tgattgggt tttgcagctt     3960 ttactctatt ttgcctcttt ttgtgttaca gctacccatt cttcggtttc gttcccctct    4020
tgggtgtatt ttctgggtct tctcggcgtg tgcgcatggg ggttttggc tgctggctgg     4080 cttttgctgt tggcctgttc aagcctgtgt ccgacccagt cggcactgct tgtgagtttg    4140
actcgccaga gtgtaggaac gtccttcatt cttttgagct tctcaaacct tgggaccctg    4200
ttcgcagcct tgttgtgggc cccgtcggtc tcggtcttgc cattcttggc aggttactgg    4260
gcggggcacg ctacatctgg catttttgc ttaggcttgg cattgttgca gattgtatct     4320
tggctggagc ttatgtgctt tctcaaggta ggtgtaaaaa gtgctgggga tcttgtataa    4380
gaactgctcc taatgaaatc gccttcaacg tgttcccttt tacacgtgcg accaggtcgt    4440
cactcatcga cctgtgcgat cggttttgtg cgccaaaagg catggacccc attttcctcg    4500
ccactgggtg gcgtgggtgc tggaccggcc gaagtcccat tgagcaaccc tctgaaaaac    4560
ccatcgcgtt cgcccagttg gatgaaaaga ggattacggc tagaactgtg gtcgctcagc    4620
cttatgatcc taatcaagcc gtaaagtgct tgcgggtgtt acaggcgggt ggggcgatgg    4680
tggccgaggc agtcccaaaa gtggtcaaag tttctgctat tccattccga gccccctttt    4740
ttcccaccgg agtgaaagtt gatcccgagt gcaggatcgt ggtcgacccc gatactttta    4800
ctacagccct ccggtctggt tactctacca caaacctcgt ccttggtgtg ggggactttg    4860
cccagctgaa tggactaaag atcaggcaaa tttccaagcc ttcggagga ggcccacacc     4920 tcattgctgc cctgcatgtt gcctgctcga tggcgttgca catgcttgct ggggtttatg    4980
```

```
taacttcagt ggggtcttgc ggtgccggca ccaacgatcc atggtgcact aatccgtttg    5040
ccgttcctgg ctacggacca ggctctctct gcacgtccag attgtgcatc tcccaacatg    5100
gccttaccct gccccttgaca gcacttgtgg cgggattcgg tcttcaggaa atcgccttgg   5160
tcgttttgat tttcgtttcc atcggaggca tggctcatag gttgagttgt aaggctgata    5220
tgctgtgcat cttacttgca atcgccagct atgtttgggt accccttacc tggttgcttt    5280
gtgtgtttcc ttgttggttg cgctggttct ctttgcaccc cctcaccatc ctatggttgg    5340
tgttttcttt gatttctgta aatatgcctt cgggaatctt ggccgtggtg ttattggttt    5400
ctctttggct tttgggacgt tatactaaca ttgctggtct tgtcaccccc tatgatattc    5460
atcattacac cagtggcccc cgcggtgttg ccgccttagc taccgcacca gatggaacct    5520
acttggctgc cgtccgccgc gctgcgttga ctggtcgcac catgctgttc accccgtctc    5580
agcttgggtc ccttcttgag ggcgctttca gaactcgaaa gccctcactg aacaccgtca    5640
atgtggttgg gtcctccatg ggctctggtg gagtgttcac catcgacggg aaaattaggt    5700
gcgtgactgc cgcacatgtc cttacgggta attcggctag ggtttccgga gtcggcttca    5760
atcaaatgct tgactttgat gtgaaagggg acttcgccat agctgattgc cgaattggc    5820 aaggagctgc tcccaagacc caattctgcg aggatggatg ggctggccgt gcctattggc    5880
tgacatcctc tggcgtcgaa cccggtgtta ttgggaatgg attcgccttc tgcttcaccg    5940
cgtgcggcga ttccgggtcc ccagtgatca ccgaagctgg tgagcttgtc ggcgttcaca    6000
caggatcaaa taaacaagga ggtggcatcg tcacgcgccc ttcaggccag ttttgtaacg    6060
tggcacccat caagctgagc gaattaagtg aattctttgc tggacccaag gtcccgctcg    6120
gtgatgtgaa ggttggcagc cacataatta agatacgtg cgaagtacct tcagatcttt    6180
gcgccttgct tgctgccaaa cctgaactgg agggaggcct ctccaccgtc caacttctgt    6240
gtgtgttttt cctactgtgg agaatgatgg gacatgcctg gacgccttg gttgctgtgg    6300 ggttttcat tctgaatgag gttctcccag ctgtcctggt tcggagtgtt ttctcctttg    6360
ggatgtttgt gctatcttgg ctcacaccat ggtctgcgca agttctgatg atcaggcttc    6420
taacagcagc tcttaacagg aacagatggt cacttgcctt ttacagcctt ggtgcggtga    6480
ccggttttgt cgcagatctt gcggcaactc aagggcaccc gttgcaggca gtaatgaatt    6540
tgagcaccta tgccttcctg cctcggatga tggttgtgac ctcaccagtc ccagtgattg    6600
cgtgtggtgt tgtgcaccta cttgccatca ttttgtactt gttcaagtac cgcggcctgc    6660
acaatgttct tgttggtgat ggagcgtttt ctgcagcttt cttcttgcga tactttgccg    6720
agggaaagtt gagggaaggg gtgtcgcaat cctgcggaat gaatcatgag tcattaactg    6780
gtgccctcgc tatgagactc aatgacgagg acttggactt ccttacgaaa tggactgatt    6840
ttaagtgctt tgtttctgcg tccaacatga ggaatgcagc aggccaattc atcgaggctg    6900
cctatgcaaa agcacttaga attgaacttg cccagttggt gcaggttgat aaggttcgag    6960
gtacttttgg caagcttgag gcttttgctg ataccgtggc accccaactc tcgcccggtg    7020
acattgttgt tgctcttggc catacgcctg ttggcagcat cttcgaccta aggttggtg    7080 gtaccaagca tactctccaa gtcattgaga ccagagtcct tgccgggtcc aaaatgaccg    7140
tggcgcgcgt cgttgaccca acccccacgc ccccacccgc accgtgccc atcccctcc     7200 caccgaaagt tctagagaat ggtcccaacg cctggggga tggggaccgt ttgaataaga    7260
agaagaggcg taggatggaa accgtcgcca tctttgtcat gggtgggaag aagtaccaga    7320 aatttggga caagaattcc ggtgatgtgt tttacgagga ggtccatgac aacacagatg    7380
```

```
cgtgggagtg cctcagagtt ggtgaccctg ccgactttga ccctgagaag ggaactctgt    7440
gtgggcatac tactattgaa gataaggatt acaaagtcta cgcctcccca tctggcaaga    7500
agttcctggt ccccgtcaac tcagagagcg aagagcccca atgggaagct gcaaagcttt    7560
ccgtggagca ggcccttggc atgatgaatg tcgacggtga actgacggcc aaagaagtgg    7620
agaaactgaa aagaataatt gacaaacttc agggcctgac taaggagcag tgtttaaact    7680
gctagccgcc agcggcttga cccgctgtgg tcgcggcggc ttggttgtta ctgagacagc    7740
ggtaaaaata gtcaaatttc acaaccggac tttcacccta gggcctgtga atttaaaagt    7800
ggccagtgag gttgagctga agacgcggt cgagcacaac caacacccgg ttgcaagacc    7860
ggttgacggt ggtgttgtgc tcctgcgttc cgcagttcct tcgcttatag atgtcctgat    7920
ctccggtgct gacgcatctc ctaagttact cgctcgtcac gggccgggga acactgggat    7980
cgatggcacg ctttgggact ttgaggccga ggccaccaaa gaggaaattg cactcagtgc    8040
gcaaataata caggcttgtg acattaggcg cggcgacgca cctgaaattg gtctccctta    8100
caagctgtac cctgttaggg gcaacccctga gcgggtaaaa ggagttttac agaatacaag    8160
gtttggagac ataccttaca aaaccccccag tgacactgga agcccagtgc acgcggctgc    8220
ctgcctcacg cccaatgcca ctccggtgac tgatgggcgc tctgtcttgg ctactaccat    8280
gccctccggt tttgaattgt atgtaccgac cattccagcg tctgtccttg attatcttga    8340
ctctaggcct gactgcccca aacagttgac agagcacggc tgtgaggatg ccgcattgag    8400
agacctctcc aagtatgact tgtccaccca aggctttgtt ttacctgggg ttcttcgcct    8460
tgtgcgtaag tacctgtttg cccatgtggg taagtgcccg cccgttcatc ggccttccac    8520
ttaccctgcc aagaattcta tggctggaat aaatgggaac aggtttccaa ccaaggacat    8580
tcagagcgtc cctgaaatcg acgttctgtg cgcacaggcc gtgcgagaaa actggcaaac    8640
tgttacccct tgtaccctca agaaacagta ttgtgggaag aagaagacta ggacaatact    8700
cggcaccaat aatttcattg cgttggccca ccgggcagcg ttgagtggtg tcacccaggg    8760
cttcatgaaa aaggcgttta actcgcccat cgccctcggg aaaaacaaat ttaaggagct    8820
acagactccg gtcttaggca ggtgccttga agctgatctt gcatcctgtg atcgatccac    8880
acctgcaatt gtccgctggt ttgccgccaa tcttctttat gaacttgcct gtgctgaaga    8940
gcacctaccg tcgtacgtgc tgaactgctg ccatgaccta ttggtcacgc agtccggcgc    9000
agtgactaag aggggtggcc tatcgtctgg cgacccgatc acttctgtgt ctaacaccat    9060
ttacagcttg gtgatatatg cacagcacat ggtgcttagt tactttaaaa gtggtcaccc    9120
tcatggcctt ctgttcctac aagaccagct gaagttcgag gacatgctca agtccaacc    9180
cctgatcgtc tattcggacg acctcgtgct gtatgccgaa tctcccacca tgccgaacta    9240
ccactggtgg gtcgaacatc tgaatttgat gctgggtttt cagacggacc aaagaagac    9300
agccataacg gactcgccat catttctagg ctgtaggata taaatggac gccagctagt    9360
ccccaaccgt gacaggatcc tcgcggccct cgcttaccat atgaaggcaa gcaatgtttc    9420
tgaatactac gccgcggcgg ctgcaatact catggacagc tgtgcttgtt tagagtatga    9480
tcctgaatgg tttgaagagc ttgtggttgg gatagcgcag tgcgcccgca aggacgcta    9540
cagctttccc ggcccgccgt tcttcttgtc catgtgggaa aaactcagat ccaatcatga    9600
ggggaagaag tccagaatgt gcgggtattg cggggcccg ctccgtacg ccactgcctg    9660
tggcctcgac gtctgtattt accacaccca cttccaccag cattgtccag tcataatctg    9720
```

-continued

| | |
|---|---|
| gtgtggccac ccggctggtt ctggttcttg tagtgagtgc aaaccccccc tagggaaagg | 9780 |
| cacaagccct ctagatgagg tgttagaaca agtcccgtat aagcctccac ggactgtaat | 9840 |
| catgcatgtg gagcagggtc tcacccctct tgacccaggc agataccaga ctcgccgcgg | 9900 |
| attagtctcc gttaggcgtg gcatcagagg aaacgaagtt gacctaccag acggtgatta | 9960 |
| tgctagcacc gccctactcc ccacttgtaa agagatcaac atggtcgctg tcgcctctaa | 10020 |
| tgtgttgcgc agcaggttca tcatcggtcc gcccggtgct gggaaaacat actggctcct | 10080 |
| tcagcaggtc caggatggtg atgtcattta cacaccgact caccagacca tgctcgacat | 10140 |
| gattagggct ttggggacgt gccggttcaa cgtcccagca ggtacaacgc tgcaattccc | 10200 |
| tgcccctcc cgtaccggcc cgtgggttcg catcctggcc ggcggttggt gtcctggtaa | 10260 |
| gaattccttc ctgatgaag cagcgtattg taatcaccttt gatgtcttga ggctccttag | 10320 |
| caaaaccacc cttacctgtc tgggagactt caaacaactc cacccagtgg gttttgattc | 10380 |
| tcattgctat gtttttgaca tcatgcctca gacccagttg aagaccatct ggagattcgg | 10440 |
| acagaacatc tgtgatgcca tccaaccaga ttacagggac aaacttgtgt ccatggtcaa | 10500 |
| cacaacccgt gtaacctaca tggaaaaacc tgtcaagtat gggcaagtcc tcacccctta | 10560 |
| ccacagggac cgagaggacg gcgccatcac aattgactcc agtcaaggcg ccacatttga | 10620 |
| tgtggttaca ctgcatttgc ccactaaaga ttcactcaac aggcaaagag cccttgttgc | 10680 |
| tatcaccagg gcaagacatg ctatctttgt gtatgaccca cacaggcaat gcagagcat | 10740 |
| gtttgatctt cctgcgaagg gcacacccgt caacctcgca gtgcaccgtg atgagcagct | 10800 |
| gatcgtactg gatagaaata ataaagaatg cacagttgct caggctatag caacggaga | 10860 |
| taaattcagg gccaccgaca agcgcgttgt agattctctc cgcgccattt gtgctgatct | 10920 |
| ggaagggtcg agctccccgc tcccaaggt cgcacacaac ttgggatttt atttctcacc | 10980 |
| tgatttgaca cagtttgcta aactcccggt agaccttgca ccccactggc ccgtggtgac | 11040 |
| aacccagaac aatgaaaagt ggccggatcg gctggttgcc agccttcgcc ctgtccataa | 11100 |
| gtatagccgt gcgtgcattg gtgccggcta tatggtgggc ccctcggtgt ttctaggcac | 11160 |
| ccctgggtc gtgtcatact acctcacaaa atttgtcaag ggcgaggctc aagtgcttcc | 11220 |
| ggagacagtc ttcagcaccg gccgaattga ggtggattgc cgggagtatc ttgatgacag | 11280 |
| ggagcgagaa gttgctgagt ccctcccaca tgccttcatt ggcgacgtca aaggcaccac | 11340 |
| cgttggggga tgtcatcatg tcacctccaa ataccttccg cgcttccttc ccaaggaatc | 11400 |
| agtcgcggta gtcgggtttt cgagccccgg gaaagccgca aaagcagtgt gcacattgac | 11460 |
| ggatgtgtac ctcccagacc ttgaggccta cctccaccca gagactcagt ctaagtgctg | 11520 |
| gaaagttatg ttggacttca aggaagttcg actgatggtc tggaaagaca agacggccta | 11580 |
| tttccaactt gaaggccgct atttccacctg gtatcagctt gcaagctacg cctcgtacat | 11640 |
| ccgtgttcct gtcaactcca cggtgtatct ggacccctgc atgggccctg ccttttgcaa | 11700 |
| cagaagagtt gtcgggtcca cccattgggg agctgacctc gcagtcaccc cttatgatta | 11760 |
| cggtgctaaa atcatcttgt ctagcgctta ccatggtgaa atgcctcctg gatacaagat | 11820 |
| tctggcgtgc gcggagttct cgctcgacga cccagtcaag tacaaacaca cctgggggtt t | 11880 |
| tgaatcggat acagcgtatc tgtatgagtt caccggaaac ggtgaggact gggaggatta | 11940 |
| caatgatgcg tttcgtgcgc gccagaaagg gaaaatttat aaggccactg ctaccagcat | 12000 |
| gaagtttttat tttcccccgg gccccgtcat tgaaccaact ttaggcctga attgaaatga | 12060 |
| aatgggggtct atacaaagcc tcttcgacaa aattggccag cttttttgtgg atgctttcac | 12120 |

```
ggaattttg gtgtccattg ttgatatcat catatttttg gccatttgt ttggcttcac    12180
catcgccggt tggctggtgg tcttttgcat cagattggtt tgctccgcgg tattccgtgc    12240
gcgccctgcc attcaccctg agcaattaca gaagatccta tgaggccttt ctttctcagt    12300
gccgggtgga cattcccacc tgggggtaa acacccttt ggggatgttt tggcaccata    12360
aggtgtcaac cctgattgat gaaatggtgt cgcgtcgaat gtaccgcatc atggaaaaag    12420
cagggcaagc tgcctggaaa caggtggtga gcgaggctac gctgtctcgc attagtagtt    12480
tggatgtggt ggctcatttt caacatcttg ccgccattga agccgagacc tgtaaatatt    12540
tggcttctcg actgcccatg ctacacaacc tgcgcatgac agggtcaaat gtaaccatag    12600
tgtataatag cactttaaat caggtgtttg ctatttttcc aaccctggt tcccggccaa    12660
agcttcatga ttttcagcaa tggctaatag ctgtacattc ctccatattt tcctctgttg    12720
cagcttcttg tactctttt gttgtgctgt ggttgcgggt tccaatgcta cgtactgttt    12780
ttggtttccg ctggttaggg gcaatttttc tttcgaactc atggtgaatt acacggtgtg    12840
tccaccttgc ctcacccgac aagcagccgc tgaggtcctt gaacccggta ggtctctttg    12900
gtgcaggata gggcatgacc gatgtgggga ggacgatcac gacgaactag ggttcatggt    12960
tccgcctggc ctctccagcg aaagccactt gaccagtgtt tacgcctggt tggcgttcct    13020
gtccttcagc tacacggccc agttccatcc cgagatattt gggataggga acgtgagtga    13080
agtttatgtt gacatcaagc accaattcat ctgcgccgtt catgacgggc agaacaccac    13140
cttgcctcgc catgacaata tttcagccgt atttcagacc tactatcaac atcaggtcga    13200
cggcggcaat tggtttcacc tagaatggct gcgtcccttc ttttcctctt ggttggtttt    13260
aaatgtttcg tggtttctca ggcgttcgcc tgcaagccat gtttcagttc gagtctttca    13320
gacatcaaaa ccaacactac cgcagcatca ggctttgttg tcctccagga catcagctgc    13380
cttaggcatg cgactcgtc cttccgacg attcgcaaaa gctctcaatg ccgcacggcg    13440
ataggacac ccgtgtatat caccatcaca gccaatgtga cagatgagaa ttacttacat    13500
tcttctgatc tcctcatgct ttcttcttgc cttttctatg cttctgagat gagtgaaaag    13560
ggattcaagg tggtgtttgg caatgtgtca ggcatcgtgg ctgtgtgtgt caactttacc    13620
agctacgtcc aacatgtcaa agagtttacc caacgctcct tggtggtcga tcatgtgcgg    13680
ctgcttcatt tcatgacacc tgagaccatg aggtgggcaa ccgttttagc ctgtctttt    13740
gccatcctac tggcaatttg aatgttcaag tatgttgggg aaatgcttga ccgcgggctg    13800
ttgctcgcga ttgctttctt tgtggtgtat cgtgccgttc tgttttgctg tgctcggcag    13860
cgccaacagc agcagcagct ctcattttca gttgatttat aacttgacgc tatgtgagct    13920
gaatggcaca gattggctgg cagaaaaatt tgattgggca gtggagactt ttgtcatctt    13980
tcccgtgttg actcacattg tttcctatgg tgcactcacc accagccatt tccttgacac    14040
agttggtctg gttactgtgt ccaccgccgg gttttatcac gggcggtatg tcttgagtag    14100
catctacgcg gtctgtgctc tggctgcgtt gatttgcttc gttattaggc ttgcgaagaa    14160
ctgcatgtcc tggcgctact cttgtaccag atataccaac ttccttctgg acactaaggg    14220
cagactctat cgtggcggt cgcccgttat catagaaaaa gggggtaagg ttgaggtcga    14280
aggtcacctg atcgacctca aaagagttgt gcttgatggt tccgtggcaa ccccttaac    14340
cagagtttca gcggaacaat ggggtcgtct ctagacgact tttgccatga tagcacggct    14400
ccacaaaagg tgcttttggc gttttccatt acctacacgc cagtaatgat atatgctcta    14460
```

-continued

| | |
|---|---|
| aaggtaagtc gcggccgact actagggctt ctgcacccttt tgatctttct gaattgtgct | 14520 |
| tttaccttcg ggtacatgac attcgagcac tttcagagca caaatagggt cgcgctcact | 14580 |
| atgggagcag tagttgcact tctttggggg gtgtactcag ccatagaaac ctggaaattc | 14640 |
| atcacctcca gatgccgttt gtgcttgcta ggccgcaagt acattctggc ccctgcccac | 14700 |
| cacgtcgaaa gtgccgcggg ctttcatccg attgcggcaa atgataacca cgcatttgtc | 14760 |
| gtccggcgtc ccggctccac tacggttaac ggcacattgg tgcccgggtt gaaaagcctc | 14820 |
| gtgttgggtg cagaaaagc tgttaaacag ggagtggtaa accttgtcaa atatgccaaa | 14880 |
| taacaacggc aagcagcaaa agaaaaagaa ggggaatggc cagccagtca atcagctgtg | 14940 |
| ccagatgctg ggtaaaatca tcgcccagca aaaccagtcc agaggcaagg gaccgggcaa | 15000 |
| gaaaagtaag aagaaaaacc cggagaagcc ccatttttcct ctagcgaccg aagatgacgt | 15060 |
| caggcatcac ttcaccccctg gtgagcggca attgtgtctg tcgtcgatcc agactgcctt | 15120 |
| taaccagggc gctggaactt gtaccctgtc agattcaggg aggataagtt acactgtgga | 15180 |
| gtttagtttg ccgacgcatc atactgtgcg cctgatccgc gtcacagcat cacccctcagc | 15240 |
| atgatgggct ggcattcttt aggcacctca gtgtcagaat tggaagaatg tgtggtggat | 15300 |
| ggcactgatt gacattgtgc ctctaagtca cctattcaat tagggcgacc gtgtgggggt | 15360 |
| aaaatttaat tggcgagaac catgcggccg caattaaaaa aaaaaaaaa aaaaaaaaa | 15420 |
| aaaaaaaaaa aaaaaaaaa aaaaaaaaa | 15450 |

<210> SEQ ID NO 2
<211> LENGTH: 7494
<212> TYPE: DNA
<213> ORGANISM: Artificial Sequence
<220> FEATURE:
<223> OTHER INFORMATION: Description of Artificial Sequence: cDNA of
      Open Reading Frame 1a of North American PRRS Virus Genome.

<400> SEQUENCE: 2

| | |
|---|---|
| atgtctggga tacttgatcg gtgcacgtgc accccccaatg ccagggtgtt tatggcggag | 60 |
| ggccaagtct actgcacacg atgtctcagt gcacggtctc tccttcctct gaatctccaa | 120 |
| gttcctgagc ttggggtgct gggcctattt tataggcccg aagagccact ccggtggacg | 180 |
| ttgccacgtg cattccccac tgtcgagtgc tcccccgccg gggcctgctg ctttctgcg | 240 |
| atctttccaa ttgcacgaat gaccagtgga aacctgaact ttcaacaaag aatggtgcgg | 300 |
| gttgcagctg agatttacag agccggccaa ctcacccctg cagttttgaa ggctctacaa | 360 |
| gtttatgaac ggggttgtcg ctggtacccc attgtcggac ctgtccctgg agtggccgtt | 420 |
| cacgccaact ccctacatgt gagtgacaaa cctttcccgg gagcaactca tgtgttaacc | 480 |
| aacctaccgc tcccgcagag gcccaagcct gaagactttt gcccttttga gtgtgctatg | 540 |
| gctgacgtct atgacattag ccatgacgcc gtcatgtatg tggccagagg gaaagtctcc | 600 |
| tgggcccctc gtggcgggga tgaagtgaaa tttgaaaccg tccccgaaga gttgaagttg | 660 |
| attgcgaacc gactccacat ctccttcccg ccccaccacg cagtggacat gtctgagttt | 720 |
| gccttcatag cccctgggag tggtgtctcc ttgcgggtcg agcaccaaca cggttgcctt | 780 |
| cccgctgata ctgtccctga agggaactgc tggtggtgct tgtttgactt gctcccaccg | 840 |
| gaagttcaga taaagaaaat tcgccgtgct aaccaatttg ctatcaaaac caagcatggt | 900 |
| gtccctggca agtacctaca gcggaggctg caagttaatg gtctccgagc agtgactgat | 960 |
| acagatggac ctattgtcgt acagtacttc tctgttaggg agagttggat ccgccacttc | 1020 |

-continued

```
agactggcgg aagaacctag cctccctggg tttgaagacc tcctcagaat aagggtagag   1080
cctaatacgt cgccattggg tggcaagggt gaaaaaatct tccggtttgg cagtcacaag   1140
tggtacggtg ctggaaagag agcaaggaga gcacgctctg gtgcaactgc cacggtcgct   1200
cactgcgctt tgcccgctcg cgaagcccag caggccaaga agctcgaggt tgccagcgcc   1260
aacagggctg agcatctcaa gtactattcc ccgcctgccg acgggaactg tggttggcac   1320
tgcatttccg ccattaccaa ccggatggtg aattccaaat ttgaaaccac tcttcccgag   1380
agagtgagac cttcagatga ctgggctact gacgaggatc ttgtgaatac catccaaatc   1440
ctcaggctcc ccgcggcctt ggacaggaac ggtgcttgtg ctggcgccaa gtacgtgctc   1500
aagctggaag gtgagcactg gaccgtctct gtgacccctg ggatgacccc ttctttgctc   1560
ccccttgaat gtgttcaggg ttgttgtgag cataagagcg gtcttggttt cccagacgtg   1620
gtcgaagttt ccggatttga ccctgcctgt cttgaccgac ttgctgagat aatgcactta   1680
cctagcagtg tcatcccagc tgctctggcc gagatgtccg acgacttcaa tcgtctggct   1740
tccccggccg ccactgtgtg gactgtttcg caattctttg cccgccacag aggaggagag   1800
catcctgacc aggtgtgctt agggaaaatt atcaacctttt gtcaggtgat tgaggaatgc   1860
tgctgttccc ggaacaaagc caaccgggct accccggaag aggttgcggc aaaagttgac   1920
cagtacctcc gtggtgcagc aagccttgga gaatgcttgg ccaagcttga gagggctcgc   1980
ccgccgagcg cgatggacac ctcctttgat tggaatgttg tgcttcctgg ggttgagacg   2040
gcggatcaga caaccaaaca gctccatgtc aaccagtgcc gcgctctggt tcctgtcgtg   2100
actcaagagc cttttggacag agactcggtc cctctgaccg ccttctcgct gtccaattgc   2160
tactaccctg cacaaggtga cgaggtccgt caccgtgaga ggctaaactc cgtgctctct   2220
aagttggagg gggttgttcg tgaggaatat gggctcacgc caactggacc tggcccgcga   2280
cccgcactgc cgaacgggct cgacgagctt aaagaccaga tggaggagga tctgctgaaa   2340
ttagtcaacg cccaggcaac ttcagaaatg atggcctggg cagccgagca ggttgatcta   2400
aaagcttggg tcaaaaatta cccacggtgg acaccgccac cccctccacc aagagttcag   2460
cctcgaaaaa cgaagtctgt caagagcttg ctagagaaca agcctgtccc tgctccgcgc   2520
aggaaggtca gatctgatta tggcagcccg attttgatgg cgacaatgt tcctaacggt   2580
tgggaagatt cgactgttgg tggtcccctt gacctttcgg caccatccga gccgatgaca   2640
cctctgagtg agcctgtact tatttccagg ccagtgacat cttttgagtgt gccggcccca   2700
gttcctgcac cgcgtagagc tgtgtctcga ccgatgacgc cctcgagtga gccaattttt   2760
gtgtctgcac tgcgacacaa atttcagcag gtggaaaaag caaatctggc ggcagcagcg   2820
ccgatgtacc aggacgaacc cttagatttg tctgcatcct cacagactga atatgggct   2880
tctcccctaa caccaccgca gaacgtgggc attctggagg taaggggca agaagctgag   2940
gaagttctga gtgaaatctc ggatattctg aatgatacca accctgcacc tgtgtcatca   3000
agcagctccc tgtcaagtgt taggatcaca cgcccaaaat actcagctca agccattatc   3060
gacttgggcg ggccctgcag tgggcacctc caaagggaaa aagaagcatg cctccgcatc   3120
atgcgtgagg cttgtgatgc ggccaagctt agtgaccctg ccacgcagga atggctttct   3180
cgcatgtggg ataggtgga catgctgact tggcgcaaca cgtctgctta ccaggcgttt   3240
cgcaccttag atggcaggtt tgggtttctc ccaaagatga tactcgagac gccgccgccc   3300
tacccgtgtg ggttttgtgat gttgcctcac acccctgcac cttccgtgag tgcagagagc   3360
gaccttacca tcggttcagt cgccactgaa gatattccac gcatcctcgg gaaaatagaa   3420
```

```
aataccggtg agatgatcaa ccagggaccc ttggcatcct ctgaggaaga accggtatac    3480
aaccaacctg ccaaagactc ccggatatcg tcgcggggt ctgacgagag cacagcagct    3540
ccgtccgcag gtacaggtgg cgccggctta tttactgatt tgccaccttc agacggcgta    3600
gatgcggacg gtgggggcc gttgcagacg gtaagaaaga aagctgaaag gctcttcgac    3660
caattgagcc gtcaggtttt taacctcgtc tcccatctcc ctgttttctt ctcacacctc    3720
ttcaaatctg acagtggtta ttctccgggt gattggggtt ttgcagcttt tactctattt    3780
tgcctctttt tgtgttacag ctacccattc ttccgttttcg ttcccctctt gggtgtattt    3840
tctggtcttt ctcggcgtgt gcgcatgggg gttttggct gctggctggc ttttgctgtt    3900
ggcctgttca agcctgtgtc cgacccagtc ggcactgctt tgagtttga ctcgccagag    3960 tgtaggaacg tccttcattc ttttgagctt ctcaaacctt gggaccctgt tcgcagcctt    4020
gttgtgggcc ccgtcggtct cggtcttgcc attcttggca ggttactggg cggggcacgc    4080
tacatctggc atttttgct taggcttggc attgttgcag attgtatctt ggctggagct    4140
tatgtgcttt ctcaaggtag gtgtaaaaag tgctggggat cttgtataag aactgctcct    4200
aatgaaatcg ccttcaacgt gttccctttt acacgtgcga ccaggtcgtc actcatcgac    4260
ctgtgcgatc ggttttgtgc gccaaaaggc atggacccca tttttcctcgc cactgggtgg    4320 cgtgggtgct ggaccggccg aagtcccatt gagcaaccct ctgaaaaacc catcgcgttc    4380
gcccagttgg atgaaaagag gattacggct agaactgtgg tcgctcagcc ttatgatcct    4440
aatcaagccg taaagtgctt gcgggtgtta caggcgggtg gggcgatggt ggccgaggca    4500
gtcccaaaag tggtcaaagt ttctgctatt ccattccgag ccccttttt tcccaccgga    4560 gtgaaagttg atcccgagtg caggatcgtg gtcgaccccg atactttac tacagccctc    4620 cggtctggtt actctaccac aaacctcgtc cttggtgtgg gggactttgc ccagctgaat    4680
ggactaaaga tcaggcaaat ttccaagcct tcgggaggag gcccacacct cattgctgcc    4740
ctgcatgttg cctgctcgat ggcgttgcac atgcttgctg ggtttatgt aacttcagtg    4800 gggtcttgcg gtgccggcac caacgatcca tggtgcacta atccgtttgc cgttcctggc    4860
tacggaccag gctctctctg cacgtccaga ttgtgcatct cccaacatgg ccttaccctg    4920
cccttgacag cacttgtggc gggattcggt cttcaggaaa tcgccttggt cgttttgatt    4980
ttcgtttcca tcggaggcat ggctcatagg ttgagttgta aggctgatat gctgtgcatc    5040
ttacttgcaa tcgccagcta tgtttgggta cccttacct ggttgctttg tgtgtttcct    5100
tgttggttgc gctggttctc tttgcacccc ctcaccatcc tatggttggt gtttttcttg    5160
atttctgtaa atatgccttc gggaatcttg gccgtggtgt tattggtttc tctttggctt    5220
ttgggacgtt atactaacat tgctggtctt gtcaccccct atgatattca tcattacacc    5280 agtgccccc gcgtgttgc cgccttagct accgcaccag atggaaccta cttggctgcc    5340
gtccgccgcg ctgcgttgac tggtcgcacc atgctgttca ccccgtctca gcttgggtcc    5400
cttcttgagg gcgctttcag aactcgaaag ccctcactga acaccgtcaa tgtggttggg    5460
tcctccatgg gctctggtgg agtgttcacc atcgacggga aaattaggtg cgtgactgcc    5520
gcacatgtcc ttacgggtaa ttcggctagg gtttccggag tcggcttcaa tcaaatgctt    5580
gactttgatg tgaaggggga cttcgccata gctgattgcc cgaattggca aggagctgct    5640
cccaagaccc aattctgcga ggatggatgg ctggccgtg cctattggct gacatcctct    5700
ggcgtcgaac ccggtgttat tgggaatgga ttcgccttct gcttcaccgc gtgcggcgat    5760
```

-continued

```
tccgggtccc cagtgatcac cgaagctggt gagcttgtcg gcgttcacac aggatcaaat   5820
aaacaaggag gtggcatcgt cacgcgccct tcaggccagt tttgtaacgt ggcacccatc   5880
aagctgagcg aattaagtga attctttgct ggacccaagg tcccgctcgg tgatgtgaag   5940
gttggcagcc acataattaa agatacgtgc gaagtacctt cagatctttg cgccttgctt   6000
gctgccaaac ctgaactgga gggaggcctc tccaccgtcc aacttctgtg tgtgtttttc   6060
ctactgtgga gaatgatggg acatgcctgg acgcccttgg ttgctgtggg gtttttcatt   6120
ctgaatgagg ttctcccagc tgtcctggtt cggagtgttt tctcctttgg gatgtttgtg   6180
ctatcttggc tcacaccatg gtctgcgcaa gttctgatga tcaggcttct aacagcagct   6240
cttaacagga acagatggtc acttgccttt tacagccttg gtgcggtgac cggttttgtc   6300
gcagatcttg cggcaactca agggcacccg ttgcaggcag taatgaattt gagcacctat   6360
gccttcctgc ctcggatgat ggttgtgacc tcaccagtcc cagtgattgc gtgtggtgtt   6420
gtgcacctac ttgccatcat tttgtacttg ttcaagtacc gcggcctgca caatgttctt   6480
gttggtgatg gagcgttttc tgcagctttc ttcttgcgat actttgccga gggaaagttg   6540
agggaagggg tgtcgcaatc ctgcggaatg aatcatgagt cattaactgg tgccctcgct   6600
atgagactca atgacgagga cttggacttc cttacgaaat ggactgattt taagtgcttt   6660
gtttctgcgt ccaacatgag gaatgcagca ggccaattca tcgaggctgc ctatgcaaaa   6720
gcacttagaa ttgaacttgc ccagttggtg caggttgata aggttcgagg tactttggcc   6780
aagcttgagg cttttgctga taccgtggca ccccaactct cgcccggtga cattgttgtt   6840
gctcttggcc atacgcctgt tggcagcatc ttcgacctaa aggttggtgg taccaagcat   6900
actctccaag tcattgagac cagagtcctt gccgggtcca aaatgaccgt ggcgcgcgtc   6960
gttgacccaa cccccacgcc cccacccgca cccgtgccca tccccctccc accgaaagtt   7020
ctagagaatg gtcccaacgc ctggggggat ggggaccgtt tgaataagaa gaagaggcgt   7080
aggatggaaa ccgtcggcat ctttgtcatg ggtgggaaga agtaccagaa attttgggac   7140
aagaattccg gtgatgtgtt ttacgaggag gtccatgaca acacagatgc gtgggagtgc   7200
ctcagagttg gtgaccctgc cgactttgac cctgagaagg gaactctgtg tgggcatact   7260
actattgaag ataaggatta caaagtctac gcctccccat ctggcaagaa gttcctggtc   7320
cccgtcaact cagagagcgg aagagcccaa tgggaagctg caaagctttc cgtggagcag   7380
gcccttggca tgatgaatgt cgacggtgaa ctgacggcca aagaagtgga gaaactgaaa   7440
agaataattg acaaacttca gggcctgact aaggagcagt gtttaaactg ctag         7494
```

<210> SEQ ID NO 3
<211> LENGTH: 4392
<212> TYPE: DNA
<213> ORGANISM: Artificial Sequence
<220> FEATURE:
<223> OTHER INFORMATION: Description of Artificial Sequence: cDNA of Open Reading Frame 1b of North American PRRS Virus Genome.

<400> SEQUENCE: 3

```
ggagcagtgt ttaaactgct agccgccagc ggcttgaccc gctgtggtcg cggcggcttg     60
gttgttactg agacagcggt aaaaatagtc aaatttcaca accggacttt caccctaggg    120
cctgtgaatt taaaagtggc cagtgaggtt gagctgaaag acgcggtcga gcacaaccaa    180
cacccggttg caagaccggt tgacggtggt gttgtgctcc tgcgttccgc agttccttcg    240
cttatagatg tcctgatctc cggtgctgac gcatctccta agttactcgc tcgtcacggg    300
```

-continued

| | |
|---|---|
| ccggggaaca ctgggatcga tggcacgctt tgggactttg aggccgaggc caccaaagag | 360 |
| gaaattgcac tcagtgcgca aataatacag gcttgtgaca ttaggcgcgg cgacgcacct | 420 |
| gaaattggtc tcccttacaa gctgtaccct gttaggggca accctgagcg ggtaaaagga | 480 |
| gttttacaga atacaaggtt tggagacata ccttacaaaa ccccagtga cactggaagc | 540 |
| ccagtgcacg cggctgcctg cctcacgccc aatgccactc cggtgactga tgggcgctct | 600 |
| gtcttggcta ctaccatgcc ctccggtttt gaattgtatg taccgaccat tccagcgtct | 660 |
| gtccttgatt atcttgactc taggcctgac tgccccaaac agttgacaga gcacggctgt | 720 |
| gaggatgccg cattgagaga cctctccaag tatgacttgt ccacccaagg ctttgtttta | 780 |
| cctgggttc ttcgccttgt gcgtaagtac ctgtttgccc atgtgggtaa gtgcccgccc | 840 |
| gttcatcggc cttccactta ccctgccaag aattctatgg ctggaataaa tgggaacagg | 900 |
| tttccaacca aggacattca gagcgtccct gaaatcgacg ttctgtgcgc acaggccgtg | 960 |
| cgagaaaact ggcaaactgt taccccttgt accctcaaga aacagtattg tgggaagaag | 1020 |
| aagactagga caatactcgg caccaataat ttcattgcgt tggcccaccg ggcagcgttg | 1080 |
| agtggtgtca cccagggctt catgaaaaag gcgtttaact cgcccatcgc cctcgggaaa | 1140 |
| aacaaattta aggagctaca gactccggtc ttaggcaggt gccttgaagc tgatcttgca | 1200 |
| tcctgtgatc gatccacacc tgcaattgtc cgctggtttg ccgccaatct tctttatgaa | 1260 |
| cttgcctgtg ctgaagagca cctaccgtcg tacgtgctga actgctgcca tgacctattg | 1320 |
| gtcacgcagt ccggcgcagt gactaagagg ggtggcctat cgtctggcga cccgatcact | 1380 |
| tctgtgtcta acaccattta cagcttggtg atatatgcac agcacatggt gcttagttac | 1440 |
| tttaaaagtg gtcaccctca tggccttctg ttcctacaag accagctgaa gttcgaggac | 1500 |
| acggacccaa agaagacagc cataacggac tcgccatcat ttctaggctg taggataata | 1680 |
| aatgacgcc agctagtccc caaccgtgac aggatcctcg cggccctcgc ttaccatatg | 1740 |
| aaggcaagca atgtttctga atactacgcc gcggcggctg caatactcat ggacagctgt | 1800 |
| gcttgtttag agtatgatcc tgaatggttt gaagagcttg tggttgggat agcgcagtgc | 1860 |
| gcccgcaagg acggctacag ctttcccggc ccgccgttct tcttgtccat gtgggaaaaa | 1920 |
| ctcagatcca atcatgaggg gaagaagtcc agaatgtgcg ggtattgcgg ggccccggct | 1980 |
| ccgtacgcca ctgcctgtgg cctcgacgtc tgtatttacc acacccactt ccaccagcat | 2040 |
| tgtccagtca taatctggtg tggccacccg gctggttctg gttcttgtag tgagtgcaaa | 2100 |
| ccccccctag ggaaaggcac aagccctcta gatgaggtgt tagaacaagt cccgtataag | 2160 |
| cctccacgga ctgtaatcat gcatgtggag cagggtctca cccctcttga cccaggcaga | 2220 |
| taccagactc gccgcggatt agtctccgtt aggcgtggca tcagaggaaa cgaagttgac | 2280 |
| ctaccagacg gtgattatgc tagcaccgcc ctactcccca cttgtaaaga gatcaacatg | 2340 |
| gtcgctgtcg cctctaatgt gttgcgcagc aggttcatca tcggtccgcc cggtgctggg | 2400 |
| aaaacatact ggctccttca gcaggtccag gatggtgatg tcatttacac accgactcac | 2460 |
| cagaccatgc tcgacatgat tagggctttg gggacgtgcc ggttcaacgt cccagcaggt | 2520 |
| acaacgctgc aattccctgc cccctcccgt accggcccgt gggttcgcat cctggccggc | 2580 |
| ggttggtgtc ctggtaagaa ttccttcctg atgaagcag cgtattgtaa tcaccttgat | 2640 |
| gtcttgaggc tccttagcaa aaccacccct acctgtctgg agacttcaa acaactccac | 2700 |
| ccagtgggtt tgattctca ttgctatgtt tttgacatca tgcctcagac ccagttgaag | 2760 |
| accatctgga gattcggaca gaacatctgt gatgccatcc aaccagatta cagggacaaa | 2820 |

-continued

| | |
|---|---|
| cttgtgtcca tggtcaacac aacccgtgta acctacatgg aaaaacctgt caagtatggg | 2880 |
| caagtcctca ccccttacca cagggaccga gaggacggcg ccatcacaat tgactccagt | 2940 |
| caaggcgcca catttgatgt ggttacactg catttgccca ctaaagattc actcaacagg | 3000 |
| caaagagccc ttgttgctat caccagggca agacatgcta tctttgtgta tgacccacac | 3060 |
| aggcaattgc agagcatgtt tgatcttcct gcgaagggca cacccgtcaa cctcgcagtg | 3120 |
| caccgtgatg agcagctgat cgtactggat agaaataata agaatgcac agttgctcag | 3180 |
| gctataggca acggagataa attcagggcc accgacaagc gcgttgtaga ttctctccgc | 3240 |
| gccatttgtg ctgatctgga agggtcgagc tccccgctcc caaggtcgc acacaacttg | 3300 |
| ggattttatt tctcacctga tttgacacag tttgctaaac tcccggtaga ccttgcaccc | 3360 |
| cactggcccg tggtgacaac ccagaacaat gaaaagtggc cggatcggct ggttgccagc | 3240 |
| cttcgccctg tccataagta tagccgtgcg tgcattggtg ccggctatat ggtgggcccc | 3480 |
| tcggtgtttc taggcacccc tggggtcgtg tcatactacc tcacaaaatt tgtcaagggc | 3540 |
| gaggctcaag tgcttccgga gacagtcttg agcaccggcc gaattgaggt ggattgccgg | 3600 |
| gagtatcttg atgacaggga gcgagaagtt gctgagtccc tcccacatgc cttcattggc | 3660 |
| gacgtcaaag gcaccaccgt tggggatgt catcatgtca cctccaaata ccttccgcgc | 3720 |
| ttccttccca aggaatcagt cgcggtagtc ggggtttcga gccccgggaa agccgcaaaa | 3780 |
| gcagtgtgca cattgacgga tgtgtacctc ccagaccttg aggcctacct ccacccagag | 3840 |
| actcagtcta agtgctggaa agttatgttg gacttcaagg aagttcgact gatggtctgg | 3900 |
| aaagacaaga cggcctattt ccaacttgaa ggccgctatt tcacctggta tcagcttgca | 3960 |
| agctacgcct cgtacatccg tgttcctgtc aactccacgg tgtatctgga ccctgcatg | 4020 |
| ggccctgccc tttgcaacag aagagttgtc gggtccaccc attggggagc tgacctcgca | 4080 |
| gtcacccctt atgattacgg tgctaaaatc atcttgtcta gcgcttacca tggtgaaatg | 4140 |
| cctcctggat acaagattct ggcgtgcgcg gagttctcgc tcgacgaccc agtcaagtac | 4200 |
| aaacacacct ggggttttga atcggataca gcgtatctgt atgagttcac cggaaacggt | 4260 |
| gaggactggg aggattacaa tgatgcgttt cgtgcgcgcc agaaagggaa aatttataag | 4320 |
| gccactgcta ccagcatgaa gttttatttt ccccgggcc ccgtcattga accaactta | 4380 |
| ggcctgaatt ga | 4392 |

<210> SEQ ID NO 4
<211> LENGTH: 771
<212> TYPE: DNA
<213> ORGANISM: Artificial Sequence
<220> FEATURE:
<223> OTHER INFORMATION: Description of Artificial Sequence: cDNA of
      Open Reading Frame 2 of North American PRRS Virus Genome.

<400> SEQUENCE: 4

| | |
|---|---|
| atgaaatggg gtctatacaa agcctcttcg acaaaattgg ccagcttttt gtggatgctt | 60 |
| tcacggaatt tttggtgtcc attgttgata tcatcatatt tttggccatt tgtttggct | 120 |
| tcaccatcgc cggttggctg gtggtctttt gcatcagatt ggtttgctcc gcggtattcc | 180 |
| gtgcgcgccc tgccattcac cctgagcaat tacagaagat cctatgaggc ctttctttct | 240 |
| cagtgccggg tggacattcc cacctggggg gtaaaacacc ctttggggat gttttggcac | 300 |
| cataaggtgt caaccctgat tgatgaaatg gtgtcgcgtc gaatgtaccg catcatggaa | 360 |
| aaagcagggc aagctgcctg gaaacaggtg gtgagcgagg ctacgctgtc tcgcattagt | 420 |

```
agtttggatg tggtggctca ttttcaacat cttgccgcca ttgaagccga gacctgtaaa    480
tatttggctt ctcgactgcc catgctacac aacctgcgca tgacagggtc aaatgtaacc    540
atagtgtata atagcacttt aaatcaggtg tttgctattt ttccaacccc tggttcccgg    600
ccaaagcttc atgattttca gcaatggcta atagctgtac attcctccat attttcctct    660
gttgcagctt cttgtactct ttttgttgtg ctgtggttgc gggttccaat gctacgtact    720
gtttttggtt tccgctggtt agggggcaatt tttctttcga actcatggtg a            771

<210> SEQ ID NO 5
<211> LENGTH: 765
<212> TYPE: DNA
<213> ORGANISM: Artificial Sequence
<220> FEATURE:
<223> OTHER INFORMATION: Description of Artificial Sequence:  cDNA of
      Open Reading Frame 3  of North American PRRS Virus Genome.

<400> SEQUENCE: 5
atggctaata gctgtacatt cctccatatt ttcctctgtt gcagcttctt gtactctttt    60
tgttgtgctg tggttgcggg ttccaatgct acgtactgtt tttggtttcc gctggttagg    120
ggcaattttt ctttcgaact catggtgaat tacacggtgt gtccaccttg cctcacccga    180
caagcagccg ctgaggtcct tgaacccggt aggtctcttt ggtgcaggat agggcatgac    240
cgatgtgggg aggacgatca cgacgaacta gggttcatgg ttccgcctgg cctctccagc    300
gaaagccact tgaccagtgt ttacgcctgg ttggcgttcc tgtccttcag ctacacggcc    360
cagttccatc ccgagatatt tgggataggg aacgtgagtg aagtttatgt tgacatcaag    420
caccaattca tctgcgccgt tcatgacggg cagaacacca ccttgcctcg ccatgacaat    480
atttcagccg tatttcagac ctactatcaa catcaggtcg acggcggcaa ttggtttcac    540
ctagaatggc tgcgtcccct tctttcctct tggttggttt taaatgtttc gtggtttctc    600
aggcgttcgc ctgcaagcca tgtttcagtt cgagtctttc agacatcaaa accaacacta    660
ccgcagcatc aggctttgtt gtcctccagg acatcagctg ccttaggcat ggcgactcgt    720
cctttccgac gattcgcaaa agctctcaat gccgcacggc gatag                   765

<210> SEQ ID NO 6
<211> LENGTH: 537
<212> TYPE: DNA
<213> ORGANISM: Artificial Sequence
<220> FEATURE:
<223> OTHER INFORMATION: Description of Artificial Sequence:  cDNA of
      Open Reading Frame 4  of North American PRRS Virus Genome.

<400> SEQUENCE: 6
atggctgcgt cccttctttt cctcttggtt ggttttaaat gtttcgtggt ttctcaggcg    60
ttcgcctgca agccatgttt cagttcgagt ctttcagaca tcaaaaccaa cactaccgca    120
gcatcaggct ttgttgtcct ccaggacatc agctgcctta ggcatggcga ctcgtccttt    180
ccgacgattc gcaaaagctc tcaatgccgc acgcgatag ggacacccgt gtatatcacc    240
atcacagcca atgtgacaga tgagaattac ttacattctt ctgatctcct catgctttct    300
tcttgccttt tctatgcttc tgagatgagt gaaaagggat tcaaggtggt gtttggcaat    360
gtgtcaggca tcgtggctgt gtgtgtcaac tttaccagct acgtccaaca tgtcaaagag    420
tttacccaac gctccttggt ggtcgatcat gtgcggctgc ttcatttcat gacacctgag    480
accatgaggt gggcaaccgt tttagcctgt cttttttgcca tcctactggc aatttga       537
```

```
<210> SEQ ID NO 7
<211> LENGTH: 603
<212> TYPE: DNA
<213> ORGANISM: Artificial Sequence
<220> FEATURE:
<223> OTHER INFORMATION: Description of Artificial Sequence:  cDNA of
      Open Reading Frame 5 of North American PRRS Virus Genome.

<400> SEQUENCE: 7
atgttgggga aatgcttgac cgcgggctgt tgctcgcgat tgctttcttt gtggtgtatc     60
gtgccgttct gttttgctgt gctcggcagc gccaacagca gcagcagctc tcattttcag    120
ttgatttata acttgacgct atgtgagctg aatggcacag attggctggc agaaaaattt    180
gattgggcag tggagacttt tgtcatcttt cccgtgttga ctcacattgt ttcctatggt    240
gcactcacca ccagccattt ccttgacaca gttggtctgg ttactgtgtc caccgccggg    300 tttttatcacg gcggtatgt cttgagtagc atctacgcgg tctgtgctct ggctgcgttg    360
atttgcttcg ttattaggct tgcgaagaac tgcatgtcct ggcgctactc ttgtaccaga    420
tataccaact tccttctgga cactaagggc agactctatc gttggcggtc gcccgttatc    480
atagaaaaag ggggtaaggt tgaggtcgaa ggtcacctga tcgacctcaa aagagttgtg    540
cttgatggtt ccgtggcaac ccctttaacc agagtttcag cggaacaatg gggtcgtctc    600
tag                                                                  603

<210> SEQ ID NO 8
<211> LENGTH: 525
<212> TYPE: DNA
<213> ORGANISM: Artificial Sequence
<220> FEATURE:
<223> OTHER INFORMATION: Description of Artificial Sequence:  cDNA of
      Open Reading Frame 6 of North American PRRS Virus Genome.

<400> SEQUENCE: 8
atggggtcgt ctctagacga cttttgccat gatagcacgg ctccacaaaa ggtgcttttg     60
gcgttttcca ttacctacac gccagtaatg atatatgctc taaaggtaag tcgcggccga    120
ctactagggc ttctgcacct tttgatcttt ctgaattgtg cttttacctt cgggtacatg    180
acattcgagc actttcagag cacaaatagg gtcgcgctca ctatgggagc agtagttgca    240
cttctttggg gggtgtactc agccatagaa acctggaaat tcatcacctc cagatgccgt    300
ttgtgcttgc taggccgcaa gtacattctg gcccctgccc accacgtcga agtgccgcg    360 ggctttcatc cgattgcggc aaatgataac cacgcatttg tcgtccggcg tcccggctcc    420
actacggtta acggcacatt ggtgcccggg ttgaaaagcc tcgtgttggg tggcagaaaa    480
gctgttaaac agggagtggt aaaccttgtc aaatatgcca ataa                     525

<210> SEQ ID NO 9
<211> LENGTH: 372
<212> TYPE: DNA
<213> ORGANISM: Artificial Sequence
<220> FEATURE:
<223> OTHER INFORMATION: Description of Artificial Sequence:  cDNA of
      Open Reading Frame 7 of North American PRRS Virus
      Genome.

<400> SEQUENCE: 9
atgccaaata caacggcaa gcagcaaaag aaaagaagg ggaatggcca gccagtcaat     60
cagctgtgcc agatgctggg taaaatcatc gcccagcaaa accagtccag aggcaaggga    120
ccgggcaaga aagtaagaa gaaaaacccg gagaagcccc attttcctct agcgaccgaa    180
```

```
gatgacgtca ggcatcactt caccctgt gagcggcaat tgtgtctgtc gtcgatccag    240 actgcctta  accagggcgc tggaacttgt accctgtcag attcagggag gataagttac   300
actgtggagt ttagtttgcc gacgcatcat actgtgcgcc tgatccgcgt cacagcatca   360
ccctcagcat ga                                                        372
```

```
<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Primer,
      forward strand, used for determining cDNA corresponding to North
      American PRRS virus genome.

<400> SEQUENCE: 10
acagtttggt gatctatg                                                   18

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:  Primer,
      reverse strand, used for determining cDNA corresponding to North
      American PRRS virus genome.

<400> SEQUENCE: 11
cagattcaga tgttcaa                                                    17

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:  Primer
      used for determining cDNA corresponding to North American PRRS
      virus genome.

<400> SEQUENCE: 12
acctcgtgct gtatgccgaa tctc                                            24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Primer,
      used for determining cDNA corresponding to North American PRRS
      virus genome.

<400> SEQUENCE: 13
tcaggcctaa agttggttca atga                                            24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Primer,
      forward strand, used for determining cDNA corresponding to North
      American PRRS virus genome.

<400> SEQUENCE: 14
gatgactggg ctactgacga ggat                                            24
```

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Primer,
      reverse strand, used for determining cDNA corresponding to North
      American PRRS virus genome.

<400> SEQUENCE: 15
agagcggctg ggatgacact g 21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer, used for determining cDNA corresponding to North American PRRS virus genome.

<400> SEQUENCE: 16
ccggggaagc cagacgattg aa 22

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer, used for determining cDNA corresponding to North American PRRS virus genome.

<400> SEQUENCE: 17
agggggagca aagaaggggt catc 24

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer forward strand, used for determining cDNA corresponding to North American PRRS virus genome.

<400> SEQUENCE: 18
agcacgctct ggtgcaactg 20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Primer, reverse strand, used for determining cDNA corresponding to North American PRRS virus genome.

<400> SEQUENCE: 19
gccgcggcgt agtattcag 19

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Primer, forward strand, used for determining cDNA corresponding to North American PRRS virus genome.

```
<400> SEQUENCE: 20
cgcgtcacag catcaccctc ag                                           22

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Primer,
      reverse strand, used for determining cDNA corresponding to North
      American PRRS virus genome.

<400> SEQUENCE: 21
cggtaggttg gttaacacat gagtt                                        25

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:  Primer,
      reverse strand, used for determining cDNA corresponding to North
      American PRRS virus genome.

<400> SEQUENCE: 22
tggctcttcg ggcctataaa ata                                          23

<210> SEQ ID NO 23
<211> LENGTH: 56
<212> TYPE: DNA
<213> ORGANISM: Artificial Sequence
<220> FEATURE:
<223> OTHER INFORMATION: Description of Artificial Sequence: Strand of
      synthetic doublestranded adapter used in pT7P129A.

<400> SEQUENCE: 23
ctagattaat taatacgact cactataggg atgacgtata ggtgttggct ctatgc       56

<210> SEQ ID NO 24
<211> LENGTH: 56
<212> TYPE: DNA
<213> ORGANISM: Artificial Sequence
<220> FEATURE:
<223> OTHER INFORMATION: Description of Artificial Sequence:  Strand of
      synthetic double-stranded adapter used in pT7P129A.

<400> SEQUENCE: 24
taattaatta tgctgagtga tatccctact gcatatccac aaccgagata cggtgc       56

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence:  Primer,
      forward strand, used in preparing pT7P129A.

<400> SEQUENCE: 25
actcagtcta agtgctggaa agttatg                                      27

<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence: Primer,
``` reverse strand, used in preparing pT7P129A.

<400> SEQUENCE: 26
gggatttaaa tatgcatttt tttttttttt tttttttaat tgcggccgca tggttctcg    59

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Primer,
      forward strand, used for synthesizing region flanking North
      American PRRS virus ORF7 upstream.

<400> SEQUENCE: 27
attagatctt gccaccatgg tggggaaatg cttgac    36

<210> SEQ ID NO 28
<211> LENGTH: 46
<212> TYPE: DNA
<213> ORGANISM: Artificial Sequence
<220> FEATURE:
<223> OTHER INFORMATION: Description of Artificial Sequence: Primer,
      reverse strand, used for synthesizing region flanking North
      American PRRS virus ORF7 upstream.

<400> SEQUENCE: 28
ctttacgcgt ttgcttaagt tatttggcgt atttgacaag gtttac    46

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence:  Primer,
      forward strand, used for synthesizing region flanking North
      American PRRS virus ORF7 downstream.

<400> SEQUENCE: 29
caacacgcgt cagcaaaaga aaagaagggg g    31

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Primer,
      reverse strand, used for synthesizing region flanking North
      American PRRS virus ORF7 downstream.

<400> SEQUENCE: 30
gcgcgttggc cgattcatta    20

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence:  Upper
      primer used in preparing pCMV-S-P129.

<400> SEQUENCE: 31
ctcgttaatt aaaccgtcat gacgtatagg tgttggc    37

<210> SEQ ID NO 32
<211> LENGTH: 3796
<212> TYPE: DNA

-continued

<210> ORGANISM: Plasmid
<220> FEATURE:
<223> OTHER INFORMATION: Description of Plasmid: pCMV-MC1

<400> SEQUENCE: 32

```
gaattcgagc ttgcatgcct gcaggtcgtt acataactta cggtaaatgg cccgcctggc      60
tgaccgccca acgaccccg cccattgacg tcaataatga cgtatgttcc catagtaacg     120
ccaataggga ctttccattg acgtcaatgg gtggagtatt tacggtaaac tgcccacttg     180
gcagtacatc aagtgtatca tatgccaagt acgcccccta ttgacgtcaa tgacggtaaa     240
tggcccgcct ggcattatgc ccagtacatg accttatggg actttcctac ttggcagtac     300
atctacgtat tagtcatcgc tattaccatg gtgatgcggt tttggcagta catcaatggg     360
cgtggatagc ggtttgactc acggggattt ccaagtctcc accccattga cgtcaatggg     420
agtttgtttt ggcaccaaaa tcaacgggac tttccaaaat gtcgtaacaa ctccgcccca     480
ttgacgcaaa tgggcggtag gcgtgtacgg tgggaggtct atataagcag agctcgttta     540
gtgaaccgtc agatcgcctg gagacgccat ccacgctgtt ttgacctcca tagaagacac     600
cgggaccgat ccagcctccg gactctagag gatccggtac tcgaggaact gaaaaaccag     660
aaagttaact ggtaagttta gtctttttgt cttttatttc aggtcccgga tccggtggtg     720
gtgcaaatca agaactgct cctcagtgga tgttgccttt acttctaggc ctgtacggaa     780
gtgttacttc tgctctaaaa gctgcggaat tgtacccgcg gccgcaagat atcgccctag     840
gaagatctcg atcgattggt accaatccgc gacccttaa ttaacagcta gcggatttaa     900
atcagggccc gggatactag tgagcggccg cggggatcca gacatgataa gatacattga     960
tgagtttgga caaaccacaa ctagaatgca gtgaaaaaaa tgctttatt gtgaaatttg    1020
tgatgctatt gctttatttg taaccattat aagctgcaat aaacaagtta acaacaacaa    1080
ttgcattcat tttatgtttc aggttcaggg ggaggtgtgg gaggtttttt cggatcctct    1140
agagtcgacc tgcaggcatg caagcttggc gtaatcatgg tcatagctgt ttcctgtgtg    1200
aaattgttat ccgctcacaa ttccacacaa catacgagcc ggaagcataa agtgtaaagc    1260
ctggggtgcc taatgagtga gctaactcac attaattgcg ttgcgctcac tgcccgcttt    1320
ccagtcggga aacctgtcgt gccagctgca ttaatgaatc ggccaacgcg cggggagagg    1380
cggtttgcgt attgggcgct cttccgcttc ctcgctcact gactcgctgc gctcggtcgt    1440
tcggctgcgg cgagcggtat cagctcactc aaaggcggta atacggttat ccacagaatc    1500
aggggataac gcaggaaaga acatgtgagc aaaaggccag caaaaggcca ggaaccgtaa    1560
aaaggccgcg ttgctggcgt ttttccatag gctccgcccc cctgacgagc atcacaaaaa    1620
tcgacgctca gtcagaggt ggcgaaaccc gacaggacta taaagatacc aggcgtttcc    1680
ccctggaagc tccctcgtgc gctctcctgt tccgaccctg ccgcttaccg gatacctgtc    1740
cgcctttctc ccttcgggaa gcgtggcgct ttctcatagc tcacgctgta ggtatctcag    1800
ttcggtgtag gtcgttcgct ccaagctggg ctgtgtgcac gaaccccccg ttcagcccga    1860
ccgctgcgcc ttatccggta actatcgtct gagtccaac ccggtaagac acgacttatc    1920
gccactggca gcagccactg gtaacaggat tagcagagcg aggtatgtag gcggtgctac    1980
agagttcttg aagtggtggc ctaactacgg ctacactaga aggacagtat ttggtatctg    2040
cgctctgctg aagccagtta ccttcggaaa aagagttggt agctcttgat ccggcaaaca    2100
aaccaccgct ggtagcggtg gtttttttgt ttgcaagcag cagattacgc gcagaaaaaa    2160
aggatctcaa gaagatcctt tgatcttttc tacggggtct gacgctcagt ggaacgaaaa    2220
```

```
ctcacgttaa gggattttgg tcatgagatt atcaaaaagg atcttcacct agatccttt     2280 aaattaaaaa tgaagtttta aatcaatcta agtatatat gagtaaactt ggtctgacag     2340
ttaccaatgc ttaatcagtg aggcacctat ctcagcgatc tgtctatttc gttcatccat    2400
agttgcctga ctccccgtcg tgtagataac tacgatacgg gagggcttac catctggccc    2460
cagtgctgca atgataccgc gagacccacg ctcaccggct ccagatttat cagcaataaa    2520
ccagccagcc ggaagggccg agcgcagaag tggtcctgca actttatccg cctccatcca    2580
gtctattaat tgttgccggg aagctagagt aagtagttcg ccagttaata gtttgcgcaa    2640
cgttgttgcc attgctacag gcatcgtggt gtcacgctcg tcgtttggta tggcttcatt    2700
cagctccggt tcccaacgat caaggcgagt tacatgatcc cccatgttgt gcaaaaaagc    2760
ggttagctcc ttcggtcctc cgatcgttgt cagaagtaag ttggccgcag tgttatcact    2820
catggttatg gcagcactgc ataattctct tactgtcatg ccatccgtaa gatgcttttc    2880
tgtgactggt gagtactcaa ccaagtcatt ctgagaatag tgtatgcggc gaccgagttg    2940
ctcttgcccg gcgtcaatac gggataatac cgcgccacat agcagaactt taaaagtgct    3000
catcattgga aaacgttctt cggggcgaaa actctcaagg atcttaccgc tgttgagatc    3060
cagttcgatg taacccactc gtgcacccaa ctgatcttca gcatctttta ctttcaccag    3120
cgtttctggg tgagcaaaaa caggaaggca aaatgccgca aaaaagggaa taagggcgac    3180
acggaaatgt tgaatactca tactcttcct ttttcaatat tattgaagca tttatcaggg    3240
ttattgtctc atgagcggat acatatttga atgtatttag aaaaataaac aataggggt     3300 tccgcgcaca tttccccgaa aagtgccacc tgacgtctaa gaaaccatta ttatcatgac    3360
attaacctat aaaaataggc gtatcacgag gccctttcgt ctcgcgcgtt tcggtgatga    3420
cggtgaaaac ctctgacaca tgcagctccc ggagacggtc acagcttgtc tgtaagcgga    3480
tgccgggagc agacaagccc gtcagggcgc gtcagcgggt gttggcgggt gtcgggctg    3540 gcttaactat gcggcatcag agcagattgt actgagagtg caccatatgc ggtgtgaaat    3600
accgcacaga tgcgtaagga gaaaataccg catcaggcgc cattcgccat tcaggctgcg    3660
caactgttgg gaagggcgat cggtgcgggc ctcttcgcta ttacgccagc tggcgaaagg    3720
gggatgtgct gcaaggcgat taagttgggt aacgccaggg ttttcccagt cacgacgttg    3780
taaaacgacg gccagt                                                    3796
```

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Strand
      from synthetic linker used in the preparation of pCMV-S-P129.

<400> SEQUENCE: 33
cgttaattaa accgactagt gc                                              22

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Strand from
      synthetic linker used in the preparation of pCMV-S-P129.

<400> SEQUENCE: 34
tcgagcaatt aatttggctg atcacgccgg  30

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Lower
      primer used in preparing pCMV-S-P129.

<400> SEQUENCE: 35
cggggacggt ttcaaatttc actt  24

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Portion of
      plasmid pCMV-S-P129, in 5'to 3' direction, immediately prior to
      P129 genome.

<400> SEQUENCE: 36
tatataagca gagctcgtta attaaaccgt catgacgtat aggtgttggc  50

<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence:Primer,
      forward, used for synthesizing upstream flanking region to ORF4

<400> SEQUENCE: 37
aggtcgacgg cggcaattgg tttcacctag agtggctgcg tcccttct  48

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence:Primer,
      reverse, used for synthesizing upstream flanking region to ORF4

<400> SEQUENCE: 38
tcttaagcat tggctgtgat ggtgatatac  30

<210> SEQ ID NO 39
<211> LENGTH: 44
<212> TYPE: DNA
<213> ORGANISM: Artificial Sequence
<220> FEATURE:
<223> OTHER INFORMATION: Description of Artificial Sequence:Primer,
      froward, used for synthesizing downstream flanking region to ORF4

<400> SEQUENCE: 39
cttcttaagt ccacgcgttt tcttcttgcc ttttctatgc ttct  44

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence:Primer,
      reverse, used for synthesizing downstream flanking region to ORF4

<400> SEQUENCE: 40

```
tgcccggtcc cttgcctct                                                  19
```

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence:Primer,
      forward, used for synthesizing downstream flanking region to ORF4

<400> SEQUENCE: 41

```
gtttacgcgt cgctccttgg tggtcg                                          26
```

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence:Primer,
      forward, used for synthesizing upstream flanking region to
      insertion site between ORF1b and ORF2

<400> SEQUENCE: 42

```
aacagaagag ttgtcgggtc cac                                             23
```

<210> SEQ ID NO 43
<211> LENGTH: 49
<212> TYPE: DNA
<213> ORGANISM: Artificial Sequence
<220> FEATURE:
<223> OTHER INFORMATION: Description of Artificial Sequence:Primer,
      reverse, used for synthesizing upstream flanking region to
      insertion site between  ORF1b and ORF2

<400> SEQUENCE: 43

```
gctttgacgc gtccccactt aagttcaatt caggcctaaa gttggttca                 49
```

<210> SEQ ID NO 44
<211> LENGTH: 82
<212> TYPE: DNA
<213> ORGANISM: Artificial Sequence
<220> FEATURE:
<223> OTHER INFORMATION: Description of Artificial Sequence:Primer,
      forward, used for synthesizing downstream flanking region to
      insertion site between  ORF1b and ORF2

<400> SEQUENCE: 44

```
gcgacgcgtg ttccgtggca acccctttaa ccagagtttc agcggaacaa tgaaatgggg     60
tctatacaaa gcctcttcga ca                                              82
```

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence:Primer,
      reverse, used for synthesizing downstream flanking region to
      insertion site between  ORF1b and ORF2

<400> SEQUENCE: 45

```
aacagaacgg cacgatacac cacaaa                                          26
```